United States Patent [19]

Nyfeler et al.

[11] Patent Number: 4,945,100
[45] Date of Patent: Jul. 31, 1990

[54] PROCESS FOR THE PREPARATION OF 1-TRIAZOLYLETHYL ETHER DERIVATIVES

[75] Inventors: Robert Nyfeler, Basel; Helmut Zondler, Bottmingen; Elmar Sturm, Aesch, all of Switzerland

[73] Assignee: Ciba-Geigy Corporation, Ardsley, N.Y.

[21] Appl. No.: 240,441

[22] Filed: Sep. 2, 1988

Related U.S. Application Data

[60] Continuation of Ser. No. 815,681, Jan. 2, 1986, abandoned, which is a division of Ser. No. 610,224, May 14, 1984, abandoned.

[30] Foreign Application Priority Data

May 19, 1983 [CH] Switzerland ............ 2730/83

[51] Int. Cl.$^5$ ............ A01N 43/653; C07D 249/08
[52] U.S. Cl. ............ 514/383; 548/267.8; 548/268.6
[58] Field of Search ............ 548/262; 514/383

[56] References Cited

U.S. PATENT DOCUMENTS

| | | | |
|---|---|---|---|
| 4,400,388 | 8/1983 | Timmler et al. | 548/262 |
| 4,610,716 | 9/1986 | Sturm et al. | 548/262 |

FOREIGN PATENT DOCUMENTS

| | | | |
|---|---|---|---|
| 047594 | 8/1981 | European Pat. Off. | 548/262 |
| 052424 | 10/1981 | European Pat. Off. | 548/262 |
| 077479 | 4/1983 | European Pat. Off. | 548/262 |
| 082340 | 6/1983 | European Pat. Off. | 548/262 |
| 2650831 | 11/1978 | Fed. Rep. of Germany | 548/262 |
| 2064520 | 6/1981 | United Kingdom | 548/262 |

*Primary Examiner*—Richard L. Raymond
*Assistant Examiner*—Patricia L. Morris
*Attorney, Agent, or Firm*—George R. Dohmann; Edward McC. Roberts

[57] ABSTRACT

Essentially, a process is described for the preparation of the 1-triazolylethyl ether derivatives, defined in claim 1, of the general formula I

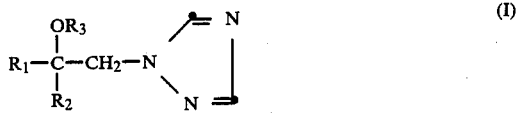

which consists in
(a) reacting an oxirane of the formula II

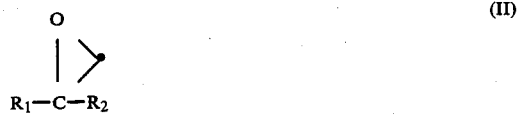

at temperatures of −20° to +100° C., in the presence of an acid catalyst or an acid condensation agent, with an alcohol of the formula III

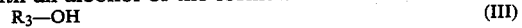

to give a glycol monoether of the formula IV

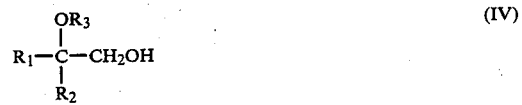

and
(b) subsequently reacting the glycol monoether of the formula IV or one of its esters, in the presence of an acid-binding agent or condensation agent, at temperatures of 0° to 150° C., with a triazole of the formula V

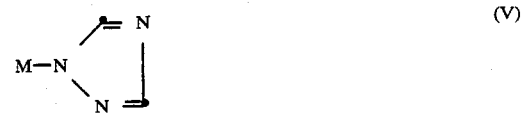

the substituents $R_1, R_2$; and $R_3$ in the formula II to IV being as defined under formula I and M in formula V being hydrogen or a metal atom. The novel compounds within the scope of formula I and their use are also described.

10 Claims, No Drawings

PROCESS FOR THE PREPARATION OF 1-TRIAZOLYLETHYL ETHER DERIVATIVES

This application is a continuation of application Ser. No. 815,681, filed Jan. 2, 1986, now abandoned, which is a divisional of application Ser. No. 610,224, filed May 14, 1984, now abandoned.

The present invention relates especially to the process described below for the preparation of 1-triazolylethyl ether derivatives of the formula I

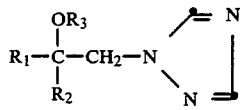

in which $R_1$ is $C_1$-$C_{12}$-alkyl, $C_1$-$C_6$-alkyl which is substituted by $C_1$-$C_6$-alkoxy or $C_3$-$C_8$-cycloalkyl, $C_3$-$C_8$-cycloalkyl, phenyl which is unsubstituted or monosubstituted to trisubstituted by halogen, $C_1$-$C_6$-halogenoalkyl, $C_1$-$C_6$-halogenoalkoxy, $C_1$-$C_6$-alkoxy, $C_1$-$C_6$-alkyl, phenoxy, halogenophenoxy, phenyl, benzyl, halogenobenzyl, nitro and/or cyano, or benzyl which is unsubstituted or monosubstituted to trisubstituted by halogen, $C_1$-$C_6$-halogenoalkyl, $C_1$-$C_6$-alkoxy, $C_1$-$C_6$-alkyl, nitro and/or cyano; $R_2$ is $C_1$-$C_{12}$-alkyl, $C_1$-$C_6$-alkyl which is substituted by $C_1$-$C_6$-alkoxy or $C_3$-$C_8$-cycloalkyl, $C_3$-$C_8$-cycloalkyl, phenyl which is unsubstituted or monosubstituted to trisubstituted by halogen, $C_1$-$C_6$-halogenoalkyl, $C_1$-$C_6$-halogenoalkoxy, $C_1$-$C_6$-alkoxy, $C_1$-$C_6$-alkyl, phenoxy, halogenophenoxy, phenyl, benzyl, halogenobenzyl, nitro and/or cyano, or benzyl which is unsubstituted or monosubstituted to trisubstituted by halogen, $C_1$-$C_6$-halogenoalkyl, $C_1$-$C_6$-alkoxy, $C_1$-$C_6$-alkyl, nitro and/or cyano; and $R_3$ is $C_1$-$C_6$-alkyl which is unsubstituted or substituted by $C_1$-$C_3$-alkoxy, or is $C_3$-$C_4$-alkenyl, benzyl or halogenobenzyl.

The term alkyl itself or as a constituent of another substituent, such as alkoxy, halogenoalkyl, halogenoalkoxy etc., is to be understood, depending on the number of carbon atoms indicated, as meaning, for example, the following linear or branched groups: methyl, ethyl, propyl, butyl, pentyl, hexyl, heptyl, octyl, nonyl, decyl, undecyl, dodecyl and the like, and isomers thereof, for example isopropyl, isobutyl, tert.-butyl, isopentyl and the like. Here and in the text which follows, the prefix halogeno in the designation of a substituent means that this substituent can be monohalogenated to perhalogenated. Halogen and halogeno represent fluorine, chlorine, bromine or iodine. Halogenoalkyl is therefore a monohalogenated to perhalogenated alkyl radical, for example $CHCl_2$, $CH_2F$, $CCl_3$, $CH_2Cl$, $CHF_2$, $CH_2CH_2Br$, $C_2Cl_5$, $CHBr_2$, $CHBrCl$ and the like, or preferably $CF_3$. Examples of alkenyl are 1-propenyl, allyl, 1-butenyl, 2-butenyl and 3-butenyl. Examples of cycloalkyl, depending on the number of carbon atoms mentioned, are cyclopropyl, cyclobutyl, cyclopentyl, cyclohexyl, cycloheptyl, cyclooctyl and the like.

An important, and therefore preferred, subgroup of microbicides is formed by compounds of the formula I in which $R_1$ and $R_2$ independently of one another are $C_1$-$C_{12}$-alkyl, $C_1$-$C_6$-alkyl which is substituted by $C_1$-$C_6$-alkoxy or $C_3$-$C_8$-cycloalkyl, $C_3$-$C_8$-cycloalkyl, phenyl, phenyl which is monosubstituted or trisubstituted by halogen, $C_1$-$C_6$-halogenoalkyl, $C_1$-$C_6$-halogenoalkoxy, $C_1$-$C_6$-alkoxy, $C_1$-$C_6$-alkyl, nitro and/or cyano, phenyl which is substituted by phenoxy, halogenophenoxy, phenyl, halogenophenyl, benzyl or halogenobenzyl, benzyl or benzyl which is monosubstituted to trisubstituted by halogen, $C_1$-$C_6$-halogenoalkyl, $C_1$-$C_6$-halogenoalkoxy, $C_1$-$C_6$-alkoxy, $C_1$-$C_6$-alkyl, nitro and/or cyano; and $R_3$ is $C_1$-$C_6$-alkyl, $C_1$-$C_6$-alkyl which is substituted by $C_1$-$C_3$-alkoxy, $C_3$-$C_4$-alkenyl, benzyl or halogenobenzyl.

Preference also attaches to microbicides of the formula I in which $R_1$ and $R_2$ independently of one another are $C_1$-$C_6$-alkyl, $C_1$-$C_2$-alkyl which is substituted by $C_1$-$C_3$-alkoxy or $C_3$-$C_6$-cycloalkyl, $C_3$-$C_6$-cycloalkyl, phenyl, phenyl which is monosubstituted to trisubstituted by halogen, $C_1$-$C_3$-halogenoalkyl, $C_1$-$C_3$-alkoxy, $C_1$-$C_3$-alkyl, nitro and/or cyano, phenyl which is substituted by phenoxy, halogenophenoxy, phenyl, benzyl or halogenobenzyl, benzyl or benzyl which is monosubstituted to trisubstituted by halogen, $C_1$-$C_3$-halogenoalkyl, methyl, methoxy, nitro and/or cyano; and $R_3$ is $C_1$-$C_4$-alkyl, $C_1$-$C_2$-alkyl which is substituted by $C_1$-$C_3$-alkoxy, $C_3$-$C_4$-alkenyl, benzyl or halogenobenzyl.

Microbicides of the formula I which are particularly preferred are those in which $R_1$ is phenyl, phenyl which is monosubstituted to trisubstituted by halogen or phenyl which is monosubstituted by phenoxy or halogenophenoxy; $R_2$ is $C_1$-$C_6$-alkyl or $C_3$-$C_7$-cycloalkyl, and $R_3$ is $C_1$-$C_6$-alkyl, $C_1$-$C_6$-alkyl which is substituted by $C_1$-$C_3$-alkoxy, $C_3$-$C_4$-alkenyl, benzyl or halogenobenzyl.

Some of the compounds of the formula I are known from the literature. Thus, for example, European Offenlegungsschrift 0,052,424 claims phytofungicidal active triazole and imidazole derivatives of the formula X

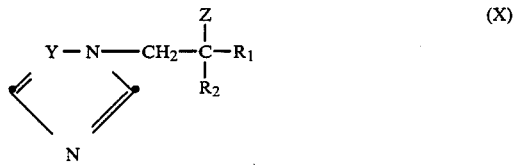

in which $R_1$ is $-CH=CH-X$, $-C\equiv C-X$ or $-CH_2CH_2X$, X being hydrogen, alkyl, hydroxyalkyl, alkoxyalkyl, cycloalkyl or aryl, aralkyl, aryloxyalkyl or heterocyclyl which is substituted or unsubstituted; $R_2$ is alkyl, cycloalkyl or substituted aryl; Z is chorine, cyano or the group $OR_3$ in which $R_3$ is hydrogen, alkyl, alkenyl or aralkyl, and Y is $=N-$ or $=CH-$, with the inclusion also of the acid addition salts and metal complexes thereof. It is suggested in the said European Offenlegungsschrift 0,052,424 that the ethers of the formula (X) [$Z=OR_3$] should be prepared by reacting the parent tertiary alcohol of the formula XI

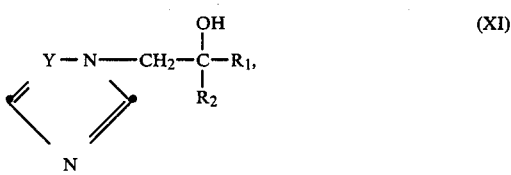

with an appropriate halide in the presence of a suitable base. Actual reaction conditions for this etherification are not disclosed.

In European Offenlegungsschrift 0,047,594 the compound 1-(1,2,4-triazol-1-yl)-bis-2-(4-fluorophenyl)-2-methoxyethane which falls within the scope of the formula I is claimed as a fungicidal and growth-regulating active ingredient. Its preparation starting from the parent tertiary alcohol is described.

Further compounds of the formula I are described as plant fungicides in European Offenlegungsschrift No. 0,082,340; these are substances of the general formula XX

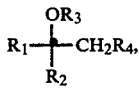
(XX)

in which $R_1$ is phenyl, phenyl which is monosubstituted or trisubstituted by halogen, $C_1$-$C_3$-halogenoalkyl, nitro, $C_1$-$C_3$-alkoxy, $C_1$-$C_8$-alkyl and/or cyano, phenyl which is substituted by phenyl or phenoxy, naphthyl, naphthyl which is monosubstituted or disubstituted by halogen, nitro and/or $C_1$-$C_3$-alkyl, benzyl or benzyl which is monosubstituted or disubstituted by halogen, nitro and/or $C_1$-$C_3$-alkyl;

$R_2$ is phenyl, phenyl whichis monosubstituted or trisubstituted by halogen, $C_1$-$C_3$-halogenoalkyl, nitro, $C_1$-$C_3$-alkoxy, $C_1$-$C_8$-alkyl and/or cyano, phenyl which is substituted by phenyl or phenoxy, or is $C_1$-$C_{10}$-alkyl, $C_3$-$C_8$-cycloalkyl or $C_3$-$C_8$-cycloalkyl-($C_1$-$C_4$-alkyl);

$R_3$ is $C_1$-$C_{12}$-alkyl, $C_2$-$C_4$-alkenyl, $C_3$-$C_4$-alkinyl, benzyl or benzyl which is monosubstituted or disubstituted by halogen, nitro and/or $C_1$-$C_3$-alkyl, and $R_4$ is an azolyl group.

Acid addition salts, quaternary azolium salts and metal complexes thereof are included.

The process described herein for the preparation of the compounds of the formula XX comprises alkylating the parent tertiary alcohol [$R_3$]=H.

The disadvantage of this known method of preparation consists in the fact that it is necessary in each case to pass through the stage of the parent tertiary alcohols. However, as is known, it is precisely the etherification of tertiary alcohols which incurs particular difficulties (for example competitive elimination reactions) because of the steric hindrance on the tertiary carbon atom, and this only affords satisfactory yields and pure end products in exceptional cases.

The present invention is therefore based on the object of indicating a novel, practicable route for the preparation of the 1-triazolylethyl ether derivatives of the formula I, which manages without the intermediate stage of the corresponding tertiary alcohols and affords the title compounds in good yields and a high state of purity.

It has now been found, surprisingly, that the 1-triazolylethyl ether derivatives of the formula I can be prepared
(a) by reacting an oxirane of the formula II

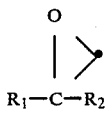
(II)

at temperatures of $-20°$ to $+100°$ C., in the presence of an acid catalyst or an acid condensation agent, with an alcohol of the formula III $$R_3—OH \qquad (III)$$

to give a glycol monoether of the formula IV

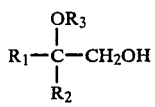
(IV)

and (b) by subsequently reacting the glycol monoether of the formula IV or one of its esters, in the presence of an acid-binding agent or condensation agent at temperatures of $0°$ to $150°$ C., with a triazole of the formula V

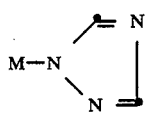
(V)

the substituents $R_1$, $R_2$ and $R_3$ in the formulae II to IV being as defined under formula I and M in formula V being hydrogen or a metal atom.

The following are examples of suitable acid catalysts or acid condensation agents:

(a) Proton acids, such as $HClO_4$, $H_2SO_4$, HCl, HF, HBr, $H_3PO_4$, alkylsulfonic acids ($CH_3SO_3H$, $C_2H_5SO_3H$, $CF_3SO_3H$, etc.), arylsulfonic acids (benzenesulfonic acid, p-bromobenzenesulfonic acid, p-toluenesulfonic acid and the like) or ion exchangers in the $H^+$ form; $HClO_4$, $H_2SO_4$ and ion exchangers are preferred.

(b) Lewis acids, such as $BF_3$, $BF_3$-etherate [$BF_3$—$(C_2H_5)_2O$], $BCl_3$, $AlCl_3$, $AlBr_3$, $SnCl_4$, $TiCl_4$, $ZnI_2$, $ZnCl_2$ etc; $BF_3$ and $BF_3$-etherate are preferred.

In general, $10^{-3}$ to 1 equivalent of catalyst or condensation agent is employed per equivalent of epoxide II, preferably 0.1 to 1 equivalent of catalyst or condensation agent.

The first partial step (a), the reaction of the oxirane II with the alcohol III, can be carried out in the presence or absence of a customary organic solvent or solvent mixture which is inert towards the reaction. Examples of possible solvents are aliphatic and aromatic hydrocarbons, such as benzene, toluene, xylenes or petroleum ether; halogenated hydrocarbons, such as chlorobenzene, methylene chloride, ethylene chloride, chloroform, carbon tetrachloride or tetrachloroethylene; ethers and ether-like compounds, such as dialkyl ethers (diethyl ether, diisopropyl ether, tert.-butyl methyl ether and the like), anisole, dioxane or tetrahydrofuran; nitriles, such as acetonitrile, propionitrile, propionitrile and the like; N,N-dimethylformamide or N,N-dimethylacetamide; dialkyl sulfoxides, such as dimethyl sulfoxide; ketones, such as acetone, diethyl ketone, methyl ethyl ketone and the like, and mixtures of such solvents with one another. Excess alcohol of the formula III is, however, particularly suitable as a solvent. The reaction temperatures are preferably between 0° and 40° C. The duration of the reaction is approx. 0.5 to 72 hours, mainly 0.5 to 16 hours.

The reaction (a) can, in principle, also be carried out without a catalyst or condensation agent, but it is then necessary to select drastic reaction conditions, in particular high temperatures, which results in numerous by-products and long reaction times and thus does not constitute an economically practicable method of preparation.

The ring-opening of an oxirane with an alkanol in accordance with the above part reaction (a) is known in principle from the literature. Thus, for example, the preparation of 2-phenyl-2-methoxyethan-1-ol in accordance with the following equation

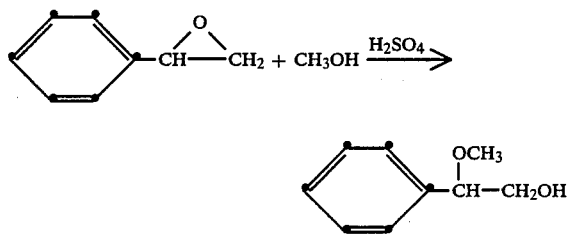

is described in [W. Reeve and I. Christoffel, J. Amer. Chem. Soc. 72, 1480 (1950)]. The preparation of further glycol monoethers of the formula IV in which $R_1=H$, $CH_3$, $CF_3$, $CH_3CHBr$ or $(CH_3)_3CCH_2$, $R_2=H$ or $CH_3$ and $R_3=CH_3$ or $C_2H_5$ from corresponding oxiranes is reported in [Epoxy Resins, Chemistry and Technology, C. A. May, Y. Tanaka, Marcel Dekker (1973)]. A suggestion that these glycol monoethers should be reacted further with 1,2,4-triazole or one of its metal salts cannot be found in any of the literature references mentioned. These references are also lacking in any indications of the use of glycol monoethers of the formula IV as intermediates for the preparation of valuable agrochemical, in particular microbicidal or growth-regulating, active ingredients.

Glycol monoethers of the formula IV in which R is $C_1$–$C_6$-alkyl which is substituted by $C_1$–$C_6$-alkoxy or $C_3$–$C_6$-cycloalkyl, $C_3$–$C_8$-cycloalkyl, phenyl, phenyl which is monosubstituted to trisubstituted by halogen, $C_1$–$C_6$-halogenoalkyl, $C_1$–$C_6$-halogenoalkoxy, $C_1$–$C_6$-alkoxy, $C_1$–$C_6$-alkyl, nitro and/or cyano, phenyl which is substituted by phenoxy, halogenophenoxy, phenyl, halogenophenyl, benzyl or halogenobenzyl, benzyl or benzyl which is monosubstituted to trisubstituted by halogen, $C_1$–$C_6$-halogenoalkyl, $C_1$–$C_6$-halogenoalkoxyl, $C_1$–$C_6$-alkoxy, $C_1$–$C_6$-alkyl, nitro and/or cyano; $R_2$ is $C_1$–$C_{12}$-alkyl or a radical indicated under $R_1$; and $R_3$ is $C_1$–$C_6$-alkyl, $C_1$–$C_6$-alkyl which is substituted by $C_1$–$C_3$-alkoxy, $C_3$–$C_4$-alkenyl, benzyl or halogenobenzyl are novel. Here and in the text which follows this important subgroup will be designated IV'. Within this group, glycol monoethers which are particularly preferred are those of the formula IV" in which $R_1$ is phenyl, phenyl which is monosubstituted to trisubstituted by halogen or phenyl which is monosubstituted by phenoxy or halogenophenoxy; $R_2$ is $C_1$–$C_6$-alkyl or $C_3$–$C_7$-cycloalkyl; and $R_3$ is $C_1$–$C_6$-alkyl, $C_1$–$C_6$-alkyl which is substituted by $C_1$–$C_3$-alkoxy, $C_3$ $C_4$-alkenyl, benzyl or halogenobenzyl.

The glycol monoethers of the formula IV' are novel and constitute intermediate products which have been specially developed for the preparation of the valuable active compounds of the formula I. By virtue of their structural nature, they can be converted easily [cf. part reaction (b)] into the compounds of the formula I. In addition, compounds of the formula IV' possess biocidal properties, in particular insecticidal and emulsifying properties.

The compounds of the formula IV', including the process of the preparing them [reaction (a)], are therefore a part of this invention.

The following are examples of typical respresentatives of the formula IV':
2-(2,4-dichlorophenyl)-2-methoxypentan-1-ol
2-(2,4-dichlorophenyl)-2-ethoxypentan-1-ol
2-(2,4-dichlorophenyl)-2-isopropoxypentan-1-ol
2-(2,4-dichlorophenyl)-2-(2-methoxyethoxy)-pentan-1-ol
2-(2,4-dichlorophenyl)-2-(2-fluorobenzyloxy)-pentan-1-ol
2-(4-fluorophenyl)-2-butoxypropan-1-ol
2-(4-fluorophenyl)-2-butoxybutan-1-ol
2-(4-fluorophenyl)-2-(buten-2-yloxy)-butan-1-ol
2-(4-chlorophenyl)-2-benzyloxypentan-1-ol
2-(2,4-dichlorophenyl)-2-methoxypropan-1-ol
2-(2,4-dichlorophenyl)-2-propoxypropan-1-ol
2-(2,4-dichlorophenyl)-2-butoxypropan-1-ol
2-(2,4-dichlorophenyl)-2-allyloxypropan-1-ol
2-(2,4-dichlorophenyl)-2-methallyloxypropan-1-ol
2-(2,4-dichlorophenyl)-2-(4-chlorobenzyloxy)-propan-1-ol
2-(2,4-dichlorophenyl)-2-methoxybutan-1-ol
2-(2,4-dichlorophenyl)-2-propoxybutan-1-ol
2-(2,4-dichlorophenyl)-2-allyloxybutan-1-ol
2-(2,4-dichlorophenyl)-2-propoxypentan-1-ol
2-(2,4-dichlorophenyl)-2-butoxypentan-1-ol
2-(2,4-dichlorophenyl)-2-allyloxypentan-1-ol
2-(2,4-dichlorophenyl)-2-(buten-2-yloxy)-pentan-1-ol
2-(2,4-dichlorophenyl)-2-benzyloxypentan-1-ol
2-(2,4-dichlorophenyl)-2-methoxy-3-methylbutan-1-ol
2-(2,4-dichlorophenyl)-2-methoxyheptan-1-ol
2-(2,4-dichlorophenyl)-2-cyclohexyl-2-methoxyethan-1-ol
2-(4-bromo-2-chlorophenyl)-2-methoxypropan-1-ol
2-(4-bromo-2-chlorophenyl)-2-methoxybutan-1-ol
2-(2-chloro-4-fluorophenyl)-2-methoxypropan-1-ol
2-(2-chloro-4-fluorophenyl)-2-methoxybutan-1-ol
2-(4-(4-chlorophenoxy)-phenyl)-2-methoxybutan-1-ol
2-(4-(4-chlorophenoxy)-phenyl)-2-methoxypropan-1-ol
2-(2-chloro-4-fluorophenyl)-2-allyloxypentan-1-ol
2-(4-bromo-2-chlorophenyl)-2-butoxypentan-1-ol
2-(4-(4-fluorophenoxy)-phenyl)-2-methoxybutan-1-ol
2-(4-(2,4-dichlorophenoxy)-phenyl)-2-methoxybutan-1-ol The second partial step in the preparation of the compounds of the formula I [reaction (b)], i.e. the reaction of a glycol monoether of the formula IV or one of its esters, is preferably carried out at temperatures between 20° and 100° C. in the presence of a condensation agent or an acid-binding agent. Examples of suitable agents of this type are tertiary amines, such as triethylamine, tripropylamine, dimethylethylamine and the like, pyridines, and pyridine bases (4-dimethylaminopyridine, 4-pyrrolidylaminopyridine and the like), oxides, hydroxides, hydrides, carbonates and bicarbonates of alkali and alkaline earth metals (CaO, BaO, NaOH, KOH, NaH, $Ca(OH)_2$, $KHCO_3$, $Ca(HCO_3)_2$, $K_2CO_3$, $Na_2CO_3$ and the like) and alkali metal acetates, such as $CH_3COONa$, $CH_3COOK$ and the like. Additionally also alkali metal alcoholates, such as $C_2H_5ONa$ ($C_3H_7$-n)ONa, $CH_3ONa$, $C_2H_5OK$ and the like, or combinations of substances, such as triphenylphosphine/dimethyl azodicarboxylate.

It can be advantageous in some cases if, instead of the free 1,2,4-triazole V (M=H), the latter is first converted into the corresponding salt, preferably an alkali metal salt and especially the sodium or potassium salt, for example by means of an alcoholate in situ, and if this salt is then reacted in the presence of one of the bases mentioned with the glycol monoether IV or one of its esters.

The reaction (b) is preferably carried out in an organic solvent which is relatively polar, but inert towards the reaction, for example pyridines, N,N-dimethylformamide, N,N-dimethylacetamide, dimethyl sulfoxide, acetonitrile, benzonitrile, hexamethylphosphoric acid triamide and others. Solvents of this type can be used in combinations with further customary solvents which are inert towards the reaction [cf. in the case of part reaction (a)], for example aliphatic or aromatic hydrocarbons, for example benzene, toluene, xylenes, hexane, petroleum ether, chlorobenzene, nitrobenzene and others.

Furthermore, it can also be advantageous if, before the reaction of IV with V, the free hydroxyl group in IV is esterified in a reactive manner and thus converted into another reactive, nucleofugic leaving group, and the resulting ester of IV is then reacted with V. In this context, here and in the text which follows, a reactive, nucleofugic leaving group is to be understood as meaning preferably substituents such as halogen: [for example fluorine, chlorine, bromine or iodine, preferably chlorine or bromine]; sulfonyloxy groups, for example fluorosulfonyloxy or preferably —OSO$_2$—R$_a$; acyloxy groups, preferably —OCO—R$_a$, and isourea radicals, preferably

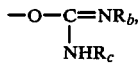

R$_a$, R$_b$ and R$_c$ independently of one another being preferably C$_1$–C$_3$-alkyl, C$_1$–C$_3$-halogenoalkyl or phenyl which is unsubstituted or substituted by halogen, methyl, nitro, trifluoromethyl and/or methoxy.

The replacement of the free hydroxyl group in the compounds of the formula IV by another reactive, nucleofugic leaving group is preferably carried out in a solvent which is inert towards the reaction. The following are examples of such solvents: aromatic and aliphatic hydrocarbons, such as benzene, toluene, xylenes, petroleum ether, ligroin or cyclohexane; halogenated hydrocarbons, such as chlorobenzene, methylene chloride, ethylene chloride, chloroform, carbon tetrachloride or tetrachloroethylene; ethers and ether-like compounds, such as diethyl ether, diisopropyl ether, t.-butylmethyl ether, dimethoxyethane, dioxane, tetrahydrofuran or anisole; esters, such as ethyl acetate, propyl acetate or butyl acetate; nitriles, such as acetonitrile, or compounds such as dimethyl sulfoxide or dimethyl formamide, and mixtures of such solvents with one another.

The introduction of the leaving group is effected by methods which are generally known. If the leaving group is chlorine, the reagent employed is, for example, phosphorus oxychloride, phosphorus trichloride, phosphorus pentachloride or preferably thionyl chloride. In general the reaction is carried out at temperatures of 0° to +120° C. If the leaving group is bromine, it is preferable to use phosphorus tribromide or phosphorus pentabromide and to carry out the reaction at 0° to +50° C.

If the leaving group is one of the groups —OSO$_2$R$_a$, —OCO—R$_a$ or

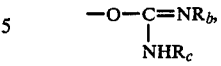

the reagent usually employed is the corresponding acid chloride or amidino-chloride. It is expedient in this case if the reaction is carried out at temperatures of −20° to +50° C., preferably −10° to +30° C., and in the presence of a weak base, such as pyridine or triethylamine.

The starting materials of the formulae II, III and V are generally known or can be prepared by methods known per se.

The process according to the invention is illustrated in greater detail by the examples quoted later in the text.

The novel triazolylethyl ether derivatives within the scope of the formula I form a further important part of the present invention.

Examples of microbicidally valuable compounds of the formula I which are novel are the following, that is to say those of the formula Ia below

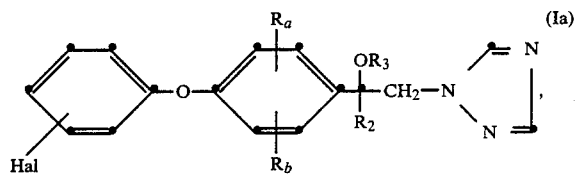

in which

Hal is halogen; R$_a$ and R$_b$ independently of one another are hydrogen, C$_1$–C$_6$-halogenoalkyl, C$_1$–C$_6$-halogenoalkoxy, C$_1$–C$_6$-alkoxy, C$_1$–C$_6$-alkyl, nitro and/or cyano; and R$_2$ and R$_3$ are as defined under formula I.

These novel compounds of the formula Ia are a part of this invention.

Within the novel compounds of the subgroup Ia, compounds of the formula I which are preferred because of their pronounced microbicidal, especially phytofungicidal, action are those in which Hal is fluorine, chlorine and/or bromine; R$_a$ and R$_b$ independently of one another are hydrogen, C$_1$–C$_3$-halogenoalkyl (preferably CF$_3$), C$_1$–C$_3$-halogenoalkoxy (preferably OCF$_3$), C$_1$–C$_3$-alkoxy, C$_1$–C$_3$-alkyl (preferably methyl or ethyl), nitro and/or cyano; R$_2$ is C$_1$–C$_6$-alkyl; and R$_3$ is C$_1$–C$_6$-alkyl (preferably C$_1$–C$_4$-alkyl), which is unsubstituted or substituted by C$_1$–C$_3$-alkoxy, or is C$_3$–C$_4$-alkenyl (preferably allyl), benzyl or halogenobenzyl.

The following are examples of representatives of the subgroup Ia which are particularly preferred:

1-(1H-1,2,4-triazol-1-yl)-2-methoxy-2-[4-(4-chlorophenoxy)phenyl]-butane;

1-(1H-1,2,4-triazol-1-yl)-2-methoxy-2-[4-(4-fluorophenoxy)phenyl]-butane;

1-(1H-1,2,4-triazol-1-yl)-2-methoxy-2-[4-(2,4-dichlorophenoxy)phenyl]-butane;

1-(1H-1,2,4-triazol-1-yl)-2-methoxy-2-[4-(4-chlorophenoxy)phenyl]-propane;

1-(1H-1,2,4-triazol-1-yl)-2-methoxy-2-[4-(4-chlorophenoxy)-2-chlorophenyl]-butane;

1-(1H-1,2,4-triazol-1-yl)-2-methoxy-2-[4-(4-chlorophenoxy)phenyl]-3-methylbutane;

1-(1H-1,2,4-triazol-1-yl)-2-allyloxy-2-[4-(4-chlorophenoxy)-2-chlorophenyl]-pentane;

1-(1H-1,2,4-triazol-1-yl)-2-methoxy-2-[4-(4-chlorophenoxy)-2-chlorophenyl]-pentane;
1-(1H-1,2,4-triazol-1-yl)-2-allyloxy-2-[4-(4-chlorophenoxy)-2-chlorophenyl]-butane;
1-(1H-1,2,4-triazol-1-yl)-2-(2-methylallyloxy)-2-[4-(4-chlorophenoxy)-2-chlorophenyl]-butane;
1-(1H-1,2,4-triazol-1-yl)-2-allyloxy-2-[4-(4-chlorophenoxy)-2-chlorophenyl]-propane;
1-(1H-1,2,4-triazol-1-yl)-2-methoxy-2-[4-(4-chlorophenoxy)-2-chlorophenyl]-propane;
1-(1H-1,2,4-triazol-1-yl)-2-methoxy-2-[4-(4-chlorophenoxy)-2-methylphenyl]-propane;
1-(1H-1,2,4-triazol-1-yl)-2-allyloxy-2-[4-(4-chlorophenoxy)-2-methylphenyl]-propane;
1-(1H-1,2,4-triazol-1-yl)-2-methoxy-2-[4-(4-chlorophenoxy-2-methylphenyl]-butane;
1-(1H-1,2,4-triazol-1-yl)-2-(2-methylpropoxy)-[4-(4-chlorophenoxy)-2-chlorophenyl]-butane;
1-(1H-1,2,4-triazol-1-yl)-2-allyloxy-2-[4-(4-chlorophenoxy)-2-methylphenyl]-pentane;
1-(1H-1,2,4-triazol-1-yl)-2-methoxy-2-[4-(4-chlorophenoxy)-2-methylphenyl]-butane;
1-(1H-1,2,4-triazol-1-yl)-2-allyloxy-2-[4-(4-chlorophenoxy)-2-methylphenyl]-butane;
1-(1H-1,2,4-triazol-1-yl)-2-propoxy-2-[4-(4-chlorophenoxy)-2-chlorophenyl]-pentane;
1-(1H-1,2,4-triazol-1-yl)-2-n-propoxy-2-[4-(4-chlorophenoxy)-2-chlorophenyl]-butane;
1-(1H-1,2,4-triazol-1-yl)-2-n-propoxy-2-[4-(4-chlorophenoxy)-2-chlorophenyl]-propane;
1-(1H-1,2,4-triazol-1-yl)-2-n-propoxy-2-[4-(4-chlorophenoxy)-2-methylphenyl]-propane.

The compounds of the formula Ia are solids, oils or mainly resins, at room temperature, which are distinguished by very valuable microbicidal properties. They can be employed preventively and curatively in the agricultural sector or related fields for controlling microorganisms which damage plants. The triazolyl derivatives within the scope of the formula I are preferred in this respect. The active ingredients, of the invention, of the formula I are distinguished by very good microbicidal activity and by problem-free application.

In addition to the process described initially, the novel compounds of the formula Ia can also be prepared by reacting a compound of the formula IIa

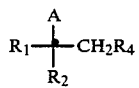

(IIa)

with a compound of the formula IIIa

R₃—W    (IIIa)

in which formulae the substituents $R_1$, $R_2$, $R_3$ and $R_4$ are as defined under formula Ia, A and W are —OH, —OM or one of the customary leaving groups and M is an alkali or alkaline earth metal atom, subject to the proviso that the reactants IIa and IIIa are always selected in such a way that either an MO— or HO— group reacts with a leaving group or two hydroxyl groups react with one another.

A customary leaving group is to be understood as meaning the leaving groups described initially.

Insofar as alcohols or alcoholates of the formula IIa are concerned (A=OH or OM), compounds of the formula Ia will in practice be prepared by customary etherification with a compound of the formula IIIa in which W is a halide, preferably a chloride or bromide. The reaction is carried out within a temperature range from 0° to 150° C., either in the absence of a solvent or, preferably, in atropic solvents, such as aromatic and aliphatic hydrocarbons, ethers and ether-like compounds (diethyl ether, dioxane, tetrahydrofuran [THF] etc.), acetonitrile, dimethylformamide [DMF] and others which are familiar to those skilled in the art of etherification reactions. Preparation by the phase transfer process can also be recommended.

Alcohols of the type of the formula IIa (A=OH) are known from the literature or can be prepared analogously to the methods described therein.

In all cases in which the substituents $R_1$ and $R_2$ in the compounds of the formula Ia are different, the compounds of the formula I possess a centre of asymmetry (*) adjacent to the oxygen group

(I)

and can therefore exist in two enantiomeric forms. In general, a mixture of both enantiomeric forms is formed when the substances are prepared. This mixture can be resolved into the optical antipodes by the customary methods of separating enantiomers, for example by fractional crystallisation of a mixture of diastereomeric salts with an optically active strong acid or by column chromatography over an optically active support and using an optically active mobile phase. The two antipodes have different microbicidal activities. Unless specially mentioned, a mixture of both enantiomeric forms is always present when a compound of the formula Ia is named.

It has been found, surprisingly, that the active substances of the formula Ia or corresponding compositions have a microbicidal spectrum, particularly against phytopathogenic fungi, which is very advantageous for practical requirements. Thus the compounds of the formula Ia possess a very advantageous curative, preventive and systemic action for the protection of plants, particularly crop plants, without affecting the latter adversely.

The active ingredients of the formula Ia make it possible to inhibit or destroy the microorganisms which occur on plants or parts of plants (fruit, flowers, foliage, stalks, tubers or roots) belonging to various useful crops, and parts of plants which grow later also remain protected from microorganism of this type.

The active ingredients of the formula Ia are effective against phytopathogenic fungi belonging to the following categories: Fungi imperfecti (for example Botrytis, Helminthosporium, Fusarium, Septoria, Cercospora and Alternaria); and Basidiomycetes (for example the genera Hemileia, Rhizoctonia and Puccinia); they are particularly effective against the category of thee Ascomycetes (for example Venturia, Podosphaera, Erysiphe, Monilinia and Uncinula). In addition the compounds of the formula I have a systemic action. They can also be employed as dressing agents for treating seed (fruits, tubers and grains) and plant cuttings to protect them against fungal infestations and can also be employed against phytopathogenic fungi which occur in the soil.

The invention also relates to compositions containing a compound of the formula Ia as at least one active substance, and to the use of the compositions or the active ingredients on their own for controlling and/or preventing attack by microorganisms.

Within the scope of this invention, the following species of plants rank as examples of target crops for the fields of indication disclosed herein: cereals: (wheat, barley, rye, oats, rice, sorghum and related crops); beet: (sugar beet and fodder beet); pome fruit, stone fruit and soft fruit: (apples, pears, plums, peaches, almonds, cherries, strawberries, raspberries and blackberries); leguminous plants: (beans, lentils, peas and soya); oil crops: (rape, mustard, poppy, olives, sunflowers, coconuts, castor oil plants, cocoa and groundnuts); curcurbitaceae: (pumpkins, cucumbers and melons); fibre plants: (cotton, flax, hemp and jute); citrus fruit: (oranges, lemons, grapefruit and mandarins); varieties of vegetables: (spinach, lettuce, asparagus, cabbage species, carrots, onions, tomatoes, potatoes and capsicums); lauraceae: (avocado, cinnamon and camphor); or plants such as maize, tobacco, nuts, coffee, sugar cane, tea, grapes, hops, banana plants and natural rubber plants. Within the scope of the present invention, plants are also, however, all species of green vegetation of other types, whether ornamental plants (composites), grassland, embankments or general low-cover crops.

Active ingredients of the formula Ia are customarily used in the form of compositions and can be applied together with further active ingredients, simultaneously or successively, to the area or plant to be treated. These further active ingredients can be either fertilisers and trace element donors or other preparations which affect plant growth. They can, however, also be selective herbicides, insecticides, fungicides, bactericides, nematocides, molluscicides or mixtures of several of these preparations, together, if appropriate, with further carriers, surfactants or other application-promoting additives which are customary in the technology of formulation.

Suitable carriers and additives can be solid or liquid and correspond to the substances which are useful in the technology of formulation, for example natural or regenerated mineral substances, solvents, dispersing agents, wetting agents, tackifiers, thickeners, binders or fertilisers.

The compounds of the formula Ia are used either in an unmodified form or preferably together with the auxiliaries customarily employed in formulation practice, and are therefore processed, in a known manner, to give, for example, emulsion concentrates, brushable pastes, directly sprayable or dilutable solutions, dilute emulsions, wettable powders, soluble powders, dusts or granules, and also encapsulations in, for example, polymeric substances. The applications processes, such as spraying, atomising, dusting, scattering, brushing or pouring, and likewise the type of composition, are selected to suit the object to be achieved and the given conditions. In general, advantageous application rates are 10 g to 5 kg of active substance (AS) per hectare; preferably 100 g to 2 kg of AS per hectare and especially 200 g to 600 g of AS per hectare.

The formulations, i.e. the compositions, preparations or combinations containing the active ingredient of the formula Ia and optionally a solid or liquid additive, are produced in a known manner, for example by intimately mixing and/or grinding the active ingredients with extenders, for example solvents, solid carriers and optionally surface-active compounds (surfactants). Those skilled in the art are familiar with these measures.

The following are suitable solvents: aromatic hydrocarbons, preferably the fractions from $C_8$ to $C_{12}$, for example mixed xylenes or substituted naphthalenes, phthalic acid esters, such as dibutyl or dioctyl phthalate, aliphatic hydrocarbons, such as cyclohexane or paraffins, alcohols and glycols and also ethers and esters thereof, such as ethanol, ethylene glycol and ethylene glycol monomethyl or monoethyl ether, ketones, such as cyclohexanone, strongly polar solvents, such as N-methyl-2-pyrrolidone, dimethyl sulfoxide or dimethyl formamide, and also optionally epoxidised vegetable oils, such as epoxidised coconut oil or soybean oil; or water.

The solid carriers used, for example for dusts and dispersible powders, are as a rule natural mineral fillers, such as calcite, talc, kaolin, montmorillonite or attapulgite. In order to improve the physical properties, it is also possible to add highly disperse silica or highly disperse absorbent polymers. Suitable granulated adsorptive carriers are porous types, for example pumice, ground brick, sepiolite or bentonite; and suitable non-sorptive carriers are materials such as calcite or sand. It is also possible to use a large number of pre-granulated materials of an inorganic or organic nature, such as, in particular, dolomite or comminuted plant residues.

Depending on the nature of the active ingredient of the formula Ia to be formulated, suitable surface-active compounds are nonionic, cationic and/or anionic surfactants having good emulsifying, dispersing and wetting properties. Surfactants are also to be understood as meaning mixtures of surfactants.

The surfactants customarily used in formulation practice are described, inter alia, in the following publications:

"Mc Cutcheon's Detergents and Emulsifiers Annual", BC Publishing Corp., Ridgewood, N.J., 1981.

Helmuth Stache "Tensid-Taschenbuch" ("Surfactants Handbook"), Carl Hanser-Verlag, Munich/Vienna 1981.

The agrochemical preparations contain, as a rule, 0.1 to 99%, in particular 0.1 to 95%, of an active ingredient of the formula I, 99.9 to 1%, in particular 99.8 to 5%, of solid or liquid additives and 0 to 25%, in particular 0.1 to 25%, of a surfactant.

Whereas commercial products are preferably in the form of concentrated compositions, the composition employed by the end user are usually diluted.

The examples which follow illustrate the invention in greater detail, without limiting it.

Preparation of the starting materials

EXAMPLE I

Preparation of

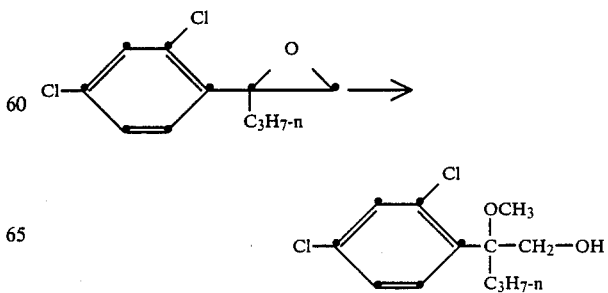

2-(2,4-dichlorophenyl)-2-methoxypentan-1-ol (a) 12.5 ml of boron trifluoride ethyl etherate are added dropwise slowly to a solution of 20.7 g (90 mmoles) of 2-(2,4-dichlorophenyl)-1,2-epoxypentane in 100 ml of absolute methanol. The temperature is kept at 18°–20° C. by occasional cooling. The temperature is then kept at 18°–20° C. for a further 6 hours, and the mixture is then stirred for a further hour at 30° C. The solution is poured into ice-cold, dilute sodium bicarbonate solution, and the resulting mixture is extracted twice with diethyl ether. The combined ether extracts are washed twice with half-saturated sodium bicarbonate solution and then twice with sodium chloride solution and are dried over sodium sulfate, filtered and concentrated. This gives 26.2 g of a yellowish, slightly viscous liquid, which is distilled in a high vacuum using a Vigreux column. The 2-(2,4-dichlorophenyl)-2-methoxypentan-1-ol thus obtained is a colourless, viscous oil of boiling point 88°–90° C./10.7×10$^{-3}$ mbar and n$^{50}_D$ 1.5322. Yield 12.1 g (=51% of theory), 100 mHz-$^1$H-NMR(CDCl$_3$): δ=7.15–7.6 ppm (m, 3H, aromatic); 4.1 ppm (dd, 2H, —CH$_2$OH); 3.25 ppm (s, 3H, —OC$\underline{H}_3$); 1.7–2.3 ppm (m, 3$\underline{H}$,

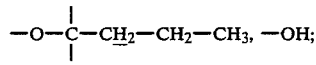

1H disappears on adding D$_2$O); 0.7–1.25 ppm (m, 5H, —CH$_2$C$\underline{H}_2$CH$_3$).

|  |  | calculated | found |
|---|---|---|---|
| analysis [%]: | C | 54.8 | 55.0 |
|  | H | 6.1 | 6.2 |
|  | Cl | 26.9 | 26.9 |

(b) A solution of 3.1 g (13.5 mmoles) of 2-(2,4-dichlorophenyl)-1,2-epoxypentane in 15 ml of absolute methanol is added dropwise at 22°–25° C. to a solution of 0.3 ml of concentrated (95–97%) sulfuric acid in 15 ml of absolute methanol, and the mixture is stirred at 22°–25° C. After 5.5 hours epoxide can no longer be detected by gas chromatography, but the desired product is detected in a yield of approx. 75%. The solution is poured into ice-cold dilute sodium bicarbonate solution, and the mixture is extracted twice with diethyl ether. The combined extracts are washed three times with half-saturated sodium chloride solution, dried over sodium sulfate, filtered and concentrated. The yield of crude product is 3.8 g of a yellowish, slightly viscous liquid. After purification by column chromatography (silica gel; 1:4 ethyl acetate/petroleum ether), 2.3 g (=65.9% of theory) of pure 2-(2,4-dichlorophenyl)-2-methoxypentan-1-ol are obtained, the data of which agree with those indicated under (a).

(c) Varying the parameters of the reaction leads to the following result:

| following result: Catalyst | Starting material [equivalents] | Reaction temperature [°C.] | Reaction time [hours] | Yield [%] |
|---|---|---|---|---|
| perchloric acid 70% | 0.5 | 0° | 86 | 75[1] |
| perchloric acid 70% | 0.5 | 20° | 22 | 80[1] |
| perchloric acid 70% | 0.5 | 20° | 22 | 70[2] |
| perchloric acid 70% | 0.5 | 65° | 0.25 | 64[1] |
| Dowex 50 W(H$^+$)® * | 0.5 | 20° | 18 | 62[1] |

[1]determined by gas chromatography, using calibration curves and an internal standard,
[2]yield of product isolated.
*a very strongly acid ion exchanger having SO$_3$H groups in the H$^+$ form.

EXAMPLE II

Preparation of

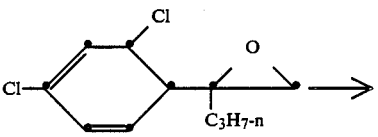

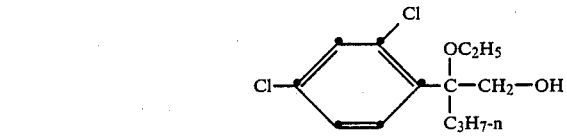

2-(2,4-dichlorophenyl)-2-ethoxy-pentan-1-ol 27.6 g (120 mmoles) of 2-(2,4-dichlorophenyl)-1,2-epoxypentane are dissolved in 60 ml of ethanol. A solution of 17.4 g (120 mmoles) of boron trifluoride-etherate in 60 ml of ethanol is added dropwise at 0° C., the internal temperature being kept at 0°–5° C. by cooling with ice water. The mixture is then left at +7° C. to react further slowly. As soon as epoxide can no longer be detected by gas chromatography, the reaction mixture is extracted with methylene chloride. The combined extracts are washed with water, dried over sodium sulfate, filtered and concentrated in vacuo. The yield of crude product is 32.3 g. Purification by column chromatography (silica gel; 4:1 petroleum ether/ethyl acetate) gives 15.96 g (53% of theory, taking into account that the epoxide employed is 90% pure). Boiling point 90° C./0.07mbar. 100 MHz-$^1$H-NMR (CDCl$_3$): δ=7.0–7.6 ppm (m, aromatic H); 3.7–4.4 ppm (m, —C$\underline{H}_2$OH); 3.2–36 ppm (q, —OC$\underline{H}_2$CH$_3$); 1.6–2.2 ppm (m, —C$\underline{H}_2$—, OH); 0.7–1.4 ppm (t, —OCH$_2$C$\underline{H}_3$ and

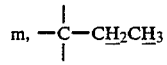

|  |  | calculated | found |
|---|---|---|---|
| analysis [%] | C | 56.3 | 56.3 |
|  | H | 6.5 | 6.8 |
|  | Cl | 25.6 | 25.6 |

EXAMPLE III

Preparation of

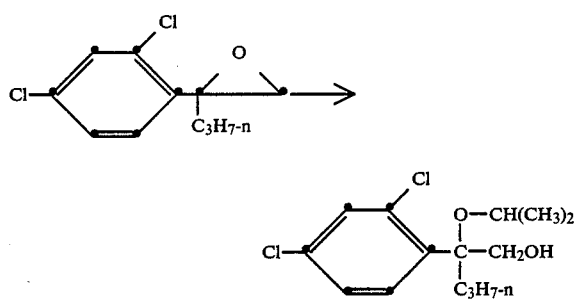

2-(2,4-dichlorophenyl)-2-isopropoxypentan-1-ol 9.3 ml (75 mmoles) of boron trifluoride-etherate are added dropwise at 20°–24° C. to a solution of 17.3 g (75 mmoles) of 2-(2,4-dichlorophenyl)-1,2-epoxypentane in 90 ml of 2-propanol. The clear solution is allowed to stand at room temperature for 24 hours and is then poured into dilute, ice-cold sodium bicarbonate solution, and the mixture is extracted twice with diethyl ether. The combined ether extracts are washed again with half-saturated sodium chloride solution, dried over sodium sulfate and filtered, and the filtrate is concentrated and purified by column chromatography (silica gel; 1:7 ethyl acetate/petroleum ether). The product is obtained in the form of a colourlesss oil. $n^{50}_D$ 1.5168. 100 MHz—$^1$H-NMR (CDCl$_3$): $\delta$=7.1–7.8 ppm (m, 3H aromatic); 3.7–4.4 ppm (m 3H, —CH$_2$—OH, —OCH(CH$_3$)$_2$); 1.5–2.3 ppm (m, 3H, —CH$_2$—CH$_2$CH$_3$, —OH, the signal of 1H disappears on adding D$_2$O); 1.25 ppm (dd, 6H, —OH(CH$_3$)$_2$); 0.8–1.4 ppm (m, 5H,

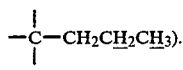
—C—CH$_2$CH$_2$CH$_3$).

|  |  | calculated | found |
|---|---|---|---|
| analysis [%] | C | 57.7 | 57.8 |
|  | H | 6.9 | 6.9 |
|  | Cl | 24.4 | 24.3 |

EXAMPLE IV

Preparation of

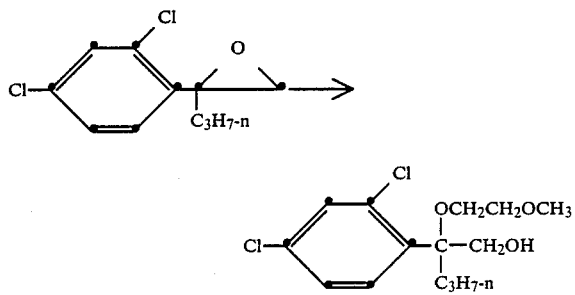

2-(2,4-dichlorophenyl)-2-(b 2-methoxyethoxy)-pentan-1-ol 2.0 ml (16.5 mmoles) of boron trifluoride ethyl etherate are added dropwise at 24°–28° C. to a solution of 3.45 g (15 mmoles) of 2-(2,4-dichlorophenyl)-1,2-epoxypentane in 60 ml of 2-methoxyethanol. The reaction solution is allowed to stand at room temperature for a further 1.75 hours and is then poured into ice-cold, dilute sodium bicarbonate solution. The mixture is extracted twice with diethyl ether. The combined ether extracts are washed twice with water and once with half-saturated sodium chloride solution, dried over sodium sulfate, filtered and concentrated. Purification by column chromatography (silica gel; 1:8 ethyl acetate/petroleum ether, then 1:4) gives 2.0 g (=43.3% of theory) of the pure product in the form of a colourless, viscous oil. $n^{50}_D$ 1.5161. 100 MHz—$^1$H—NMR (CDCl$_3$): $\delta$=7.1–7.6 ppm (m, 3H aromatic); 4.05 ppm (dd, 2H, —CH$_2$—OH); 3.2–3.7 ppm (m, 8H, —OCH$_2$CH$_2$O—CH$_3$, —OH, 1H disappears after adding D$_2$O); 1.7–2.4 ppm

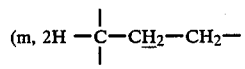
(m, 2H —C—CH$_2$—CH$_2$—

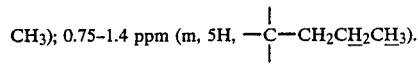
CH$_3$); 0.75–1.4 ppm (m, 5H, —C—CH$_2$CH$_2$CH$_3$).

|  |  | calculated | found |
|---|---|---|---|
| analysis [%] | C | 54.7 | 55.1 |
|  | H | 6.6 | 6.7 |
|  | Cl | 23.1 | 22.5 |

EXAMPLE V

Preparation of

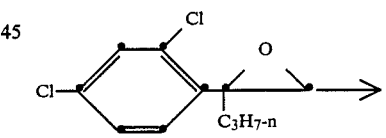

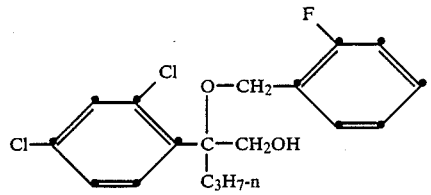

2-(2,4-dichlorophenyl)-2-(2-fluorobenzyloxy)-pentan-1-ol

A mixture of 11.6 g (92 mmoles) of 2-fluorobenzyl alcohol and 21.9 g (92 mmoles) of 2-(2,4-dichlorophenyl)-1,2-epoxypentane is added dropwise at 0°–2° C. to a solution of 2.0 ml (16.5 mmoles) of boron trifluoride ethyl etherate in 10 ml of diethyl ether. The solution is allowed to react further overnight at +7° C. and is worked up as in Example I by extraction and column chromatography. 2.95 g of the pure product are obtained in the form of a colourless oil. 100 MHz-$^1$H-NMR (CDCl$_3$): δ=6.8–7.7 ppm (m, 7H aromatic); 4.5 ppm (s, 2H,

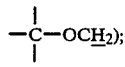

3.9–4.4 ppm (m, 2H, —C$\underline{H}_2$OH); 1.7–2.3 ppm (m, 3H, —C$\underline{H}_2$CH$_2$CH$_3$ and O$\underline{H}$); 0.7–1.4 ppm (m, 5H, —C$\underline{H}_2$C$\underline{H}_3$).

|  |  | calculated | found |
|---|---|---|---|
| analysis [%] | C | 60.5 | 60.4 |
|  | H | 5.4 | 5.5 |
|  | F | 5.3 | 5.3 |
|  | Cl | 19.9 | 19.6 |

EXAMPLE VI

Preparation of

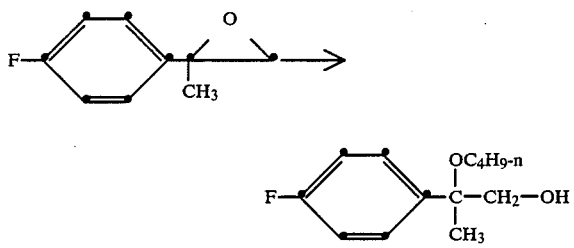

2-(4-fluorophenyl)-2-(n-butoxy)-propan-1-ol

A solution of 4.56 g (30 mmoles) of 2-(4-fluorophenyl)-1,2-epoxypropane in 5.55 g (75 mmoles) of n-butanol is added dropwise slowly at an internal temperature of 5°–7° C., with cooling, to a solution of 2.13 g (0.016 mole) of boron trifluoride ethyl etherate in 5.55 g (75 mmoles) of n-butanol, and the temperature is kept at +7° C. for a further 4 hours. The reaction mixture is then worked up by extraction (methylene chloride) and washing with water. The organic phase is dried over sodium sulfate, filtered and concentrated in vacuo. Distillation of the crude product gives 4.48 g (=66% of theory) of the pure end product in the form of a colourless oil. Boiling point 120°–125° C./20 mbar. 100 MHz-$^1$H-NMR (CDCl$_3$): δ=6.8–7.5 ppm (m, 4H aromatic); 3.5 ppm (q, 2H, —C$\underline{H}_2$OH); 3.2 ppm (m, 2H, —OC$\underline{H}_2$—); 2.3 ppm (broad, 1H, —O$\underline{H}$); 1.6 ppm (s, 3H, —C$\underline{H}_3$); 1.4 ppm (m, 4H, —C$\underline{H}_2$C$\underline{H}_2$—); 0.9 ppm (t, 3H, —C$\underline{H}_3$).

|  |  | calculated | found |
|---|---|---|---|
| analysis [%] | C | 69.0 | 69.2 |
|  | H | 8.5 | 8.3 |
|  | F | 8.4 | 8.5 |

EXAMPLE VII

Preparation of

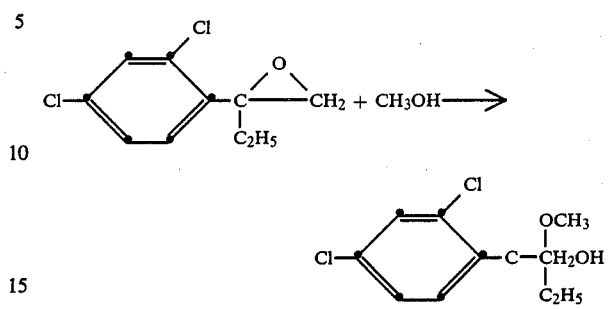

2-(2,4-dichlorophenyl)-2-methoxybutan-1-ol 10.64 g of boron trifluoride-etherate, dissolved in 30 ml of methanol, are added dropwise at 4°–6° C. to a solution of 16.25 g (75 mmoles) of 2-(2,4-dichlorophenyl)-1,2-epoxybutane of purity 95%, in 30 ml of methanol. The clear solution is then allowed to reach room temperature (20° C.) in a water bath and, after 16 hours, is worked up by extraction with water and chloroform. The chloroform solution is washed with NaHCO$_3$ and dried with Na$_2$SO$_4$, and the solvent is removed on a rotary evaporator. This gives 19 g of crude product, which is purified by chromatography, using silica gel and a mixture of 4 parts of petroleum ether and one part of ethyl acetate. Removing the solvent at 60° C. in vacuo (20 mbar) gives 13.35 g (75.2%) of pure product in the form of a colourless oil. 60 MHz-$^1$H-NMR (DCCl$_3$): δ=7.1–7.6 ppm (m, 3H, aromatic); 3.7–4.6 ppm (m, —C$\underline{H}_2$OH); 3.28 ppm (s, OC$\underline{H}_3$); 1.6–2.3 ppm (m, C$\underline{H}_2$CH$_3$, OH); 0.67 ppm (t, CH$_2$C$\underline{H}_3$).

EXAMPLE VIII

Preparation of

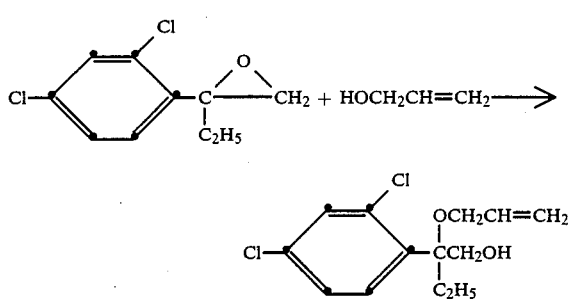

2-(2,4-dichlorophenyl)-2-allyloxybutan-1-ol 8.68 g (38 mmoles) of 2-(2,4-dichlorophenyl)-1,2-epoxybutane of 95% purity are added dropwise at 7°–8° C. to a solution of 5.67 g (40 mmoles) of boron trifluoride-etherate in 23.2 g (400 mmoles) of allyl alcohol. The mixture is kept at 20° C. overnight in a water bath, and the solution is extracted with chloroform and water. Drying the organic phase with Na$_2$SO$_4$ and removing the solvent on a rotary evaporator gives 11.3 g of crude product, which is purified by column chromatography (silica gel; mobile phase: 4 parts of petroleum ether/1 part of ethyl acetate). The yield of pure product is 5.28 g (50.5% of theory) of a colourless oil. Refractive index $n^{50}_D$=1.5291. 60 MHz-$^1$H-NMR(DCCl$_3$):

δ=7.1-7.6 ppm (m, 3H, aromatic); 5.0-6.5 ppm (m, 3H; olefinic): 3.8-4.4 ppm (m, 4H; 2×OCH₂) 1.5-2.5 ppm (m; 3H C$\underline{H}$₂CH₃, OH); 0.67 ppm (t, 3$\overline{H}$, CH₂C$\underline{H}$₃).

EXAMPLE IX

Preparation of

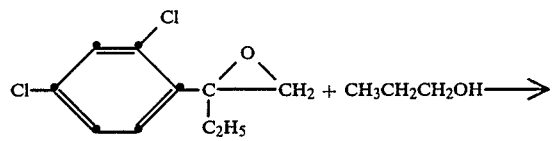

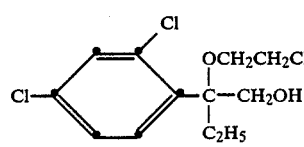

2-(2,4-dichlorophenyl)-2-propoxybutan-1-ol 8.68 g (0.04 mole) of 2-(2,4-dichlorophenyl)-1,2-epoxybutane of 95% purity are dissolved in 12 g (0.2 mole) of n-propanol, and a solution of 5.68 g (0.04 mole) of boron trifluoride-etherate in 12 g (0.2 mole) of n-propanol is added dropwise at 20° C. After 24 hours, the mixture is extracted with chloroform, the solvent is removed on a rotary evaporator and the residue is purified by column chromatography using silica gel. The yield is 5.41 g (48.8%) of a colourless oil. 60 MHz-¹H-NMR (DCCl₃): δ=7.0-7.6 ppm (m, 3H, aromatic); 3.7-4.4 ppm (m, 2H, C$\underline{H}$₂OH); 3.3 ppm (t, 2H, OC$\underline{H}$₂CH₂—); 1.4-2.6 (m, 5H, 2×C$\underline{H}$₂, O$\underline{H}$); 0.5-1.3 ppm (m, 6H, 2×C$\underline{H}$₃).

|  |  | calculated | found |
|---|---|---|---|
| analysis [%] | C | 56.33 | 56.69 |
|  | H | 6.55 | 6.62 |
|  | Cl | 25.58 | 25.18 |

EXAMPLE X

Preparation of

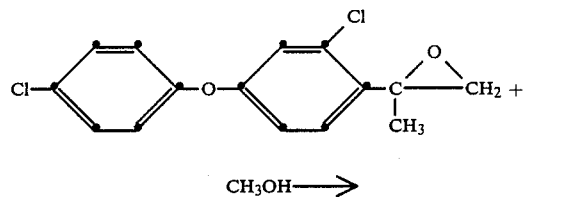

CH₃OH⟶

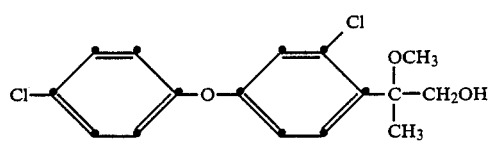

2-[2-chloro-4-(4-chlorophenoxy)-phenyl]-2-methoxy-propan-1-ol 10.0 g (0.034 mole) of 2-[2-chloro-4-(4-chlorophenoxy)phenyl]-1,2-epoxypropane are dissolved in 30 ml of methanol at room temperature and are reacted by adding 10 drops of a solution of 4.8 g of boron trifluoride-etherate in 10 ml of methanol. The temperature is kept below 25° C. by cooling in ice; epoxide can no longer be detected in a thin layer chromatogram after only 10 minutes. Working up the crude product by extraction with water and chloroform, followed by column chromatography (silica gel; 4 parts of petroleum ether/1 part of ethyl acetate) gives 9.37 g (84.5%) of pure product in the form of a colourless oil. 60 MHz-¹H-NMR (DCCl₃): δ=6.7-7.6 ppm (m, 7H, aromatic); 3.7-4.2 ppm (m, 2H, OC$\underline{H}$₂); 3.2 ppm (s, 3H, OC$\underline{H}$₃); 2.1-2.4 ppm (t, 1H, O$\underline{H}$); 1.7 ppm (s, 3H, C$\underline{H}$₃).

|  |  | calculated | found |
|---|---|---|---|
| analysis [%] | C | 58.73 | 59.36 |
|  | H | 4.93 | 5.18 |
|  | Cl | 21.67 | 21.04 |

Preparation of the end products

EXAMPLE 1

Preparation of

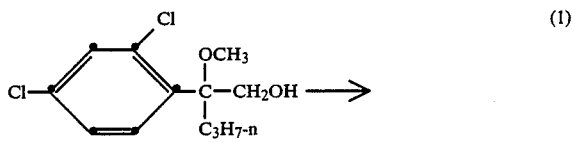 (1)

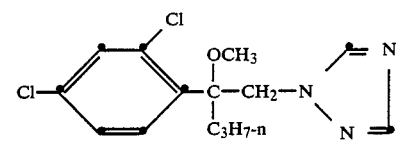

1-(1H-1,2,4-triazol-1-yl)-2-methoxy-2-(2,4-dichlorophenyl)pentane (a) Preparation of the intermediate 1-(methylsulfonyloxy)-2-methoxy-2-(2,4-dichlorophenyl)-pentane 1.6 ml (21 mmoles) of methanesulfochloride are added dropwise at 20°-25° C. to a solution of 4.2 g (16 mmoles) of 2-(2,4-dichlorophenyl)-2-methoxypentan-1-ol and 0.1 g of 4-dimethylaminopyridine in 50 ml of pyridine. After a short time colourless crystals begin to separate out. The solution is allowed to stand for 16 hours and is then poured into ice-water and extracted twice with diethyl ether. The combined ether extracts are washed twice with water and twice with ice-cold, dilute hydrochloric acid and also with half-saturated sodium chloride solution, dried over sodium sulfate, filtered and concentrated. The crude product obtained in this way can be employed in the next stage without further purification. A small sample of the crude product is purified by column chromatography (silica gel; 1:4 ethyl acetate/petroleum ether) for characterisation. A colourless oil is obtained; $n^{50}_D$ 1.5197. 100 MHz-¹H-NMR (CDCl₃): δ=7.2-7.7 ppm (m, 3H, aromatic); 4.75 ppm (dd, 2H, —C$\underline{H}$₂—OSO₂CH₃); 3.35 ppm (s, 3H, —OC$\underline{H}$₃); 2.9 ppm (s, 3H, C$\underline{H}$₃SO₂); 1.8-2.4 ppm $$\text{(m, 2H, } -\overset{|}{\underset{|}{C}}-C\underline{H}_2-CH_2CH_3);$$

0.8-1.4 ppm (m, 5H, —CH₂—C$\underline{H}$₂CH₃).

| analysis [%] | | calculated | found |
|---|---|---|---|
| | C | 45.8 | 46.0 |
| | H | 5.3 | 5.4 |
| | S | 9.4 | 9.3 |
| | Cl | 20.8 | 20.7 |

(b) Preparation of the end product

The crude product prepared in (a) is dissolved in 50 ml of absolute dimethyl sulfoxide, and 2.2 g (24 mmoles) of the sodium salt of 1,2,4-triazole are added. The reaction mixture is stirred for 16 hours at a bath temperature of 120° C. The resulting dark solution is cooled to room temperature, poured into ice water and extracted twice with ethyl acetate. The combined extracts are washed four times with half-saturated sodium chloride solution, dried over sodium sulfate, filtered and concentrated. The crude product is purified by colum chromatography (silica gel; 1:1 ethyl acetate/petroleum ether) and affords 3.2 g (=64% of theory) of a colourless oil. Boiling point 170°-175° C./0.04 mbar. 60 MHz-$^1$H-NMR (CDCl$_3$): $\delta$=7.75 and 7.60 ppm (2s, 2H of the triazole); 6.9-7.5 ppm (m, 3H, aromatic); 4.8 ppm (4 lines AB spectrum, 2H, C$\underline{H}_2$N); 3.4 ppm (s, 3H, OC$\underline{H}_3$); 1.7-2.5

(m, 2H, O—C̲—C̲H$_2$);

0.7-1.5 ppm (m, 5H, C$\underline{H}_2$C$\underline{H}_3$).

EXAMPLE 2

Preparation of

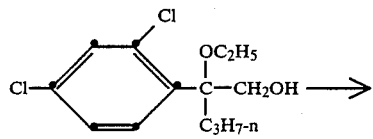

(2)

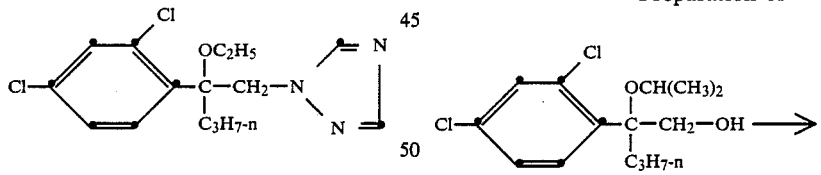

1-(1H-1,2,4-triazol-1-yl)-2-ethoxy-2-(2,4-dichlorophenyl)pentane (a) Preparation of the intermediate 1-(methylsulfonyloxy)-2-ethoxy-2-(2,4-dichlorophenyl)-pentane 6.93 g (25 mmoles) of 2-(2,4-dichlorophenyl)-2-ethoxy-pentan-1-ol are dissolved in 20 ml of pyridine and converted into the corresponding mesylate by adding 3.15 g (27.5 mmoles) of methanesulfochloride. The reaction takes place exothermically with the precipitation of pyridine hydrochloride. After a reaction time of 1 hour, water is added and the mixture is extracted with diethyl ether. The combined extracts are washed with half-saturated sodium chloride solution, dried over sodium sulfate, filtered and freed from solvent in vacuo. Yield 8.6 g. 100 MHz-$^1$H-NMR (CDCl$_3$): $\delta$=4.7 ppm (d, 2H, —C̲—C̲H$_2$OSO$_2$—);

3.2-3.6 ppm (q, 2H, —OC$\underline{H}_2$CH$_3$); 2.8 ppm (s, 3H, —OSO$_2$C$\underline{H}_3$); 1.8-2.5 ppm (m, 2H, —C$\underline{H}_2$CH$_2$CH$_3$); 1.3 ppm (t, 3H, —OCH$_2$C$\underline{H}_3$); 0.7-1.3 ppm (m, 5H, —CH$_2$C$\underline{H}_2$C$\underline{H}_3$).

(b) Prepration of the end product

The mesylate prepared in accordance with (a) is reacted with the sodium salt of 1,2,4-triazole. This is effected by dissolving 0.83 g of sodium in 30 ml of methanol, adding 2.5 g of 1,2,4-triazole and removing the solvent in vacuo. A solution of 8.55 g of the mesylate in 30 ml of dimethyl sulfoxide is added to the residual sodium salt. After being heated for 5 hours on a bath at 120° C., the mixture is cooled to room temperature and extracted with diethyl ether. The combined extracts are washed with water, dried over sodium sulfate and concentrated in vacuo. Yield of crude product 7.6 g. The crude product is purified by column chromatography (silica gel; 1:4 ethyl acetate/petroleum ether) and affords a colourless oil, which crystallises after a few days. Recrystallisation from 16 ml of petroleum ether gives 3.7 g of the end product. Melting point 67° C. 100 MHz-$^1$H-NMR (CDCl$_3$): $\delta$=7.63 and 7.72 ppm (s, 2H of triazole); 7.0-7.4 ppm (m, 3H, aromatic); 4.8 ppm (m, 2H, —C$\underline{H}_2$N); 3.2-3.8 ppm (m, 2H, —OC$\underline{H}_2$—CH$_3$); 1.7-2.4 ppm (m, 2H, —C$\underline{H}_2$CH$_2$CH$_3$); 1.3 ppm (t, 3H, —OCH$_2$C$\underline{H}_3$); 0.7-1.4 ppm (m, 5H, —CH$_2$C$\underline{H}_2$C$\underline{H}_3$).

| analysis [%] | | calculated | found |
|---|---|---|---|
| | C | 54.9 | 55.0 |
| | H | 5.8 | 5.9 |
| | N | 12.8 | 12.9 |
| | Cl | 21.6 | 21.8 |

EXAMPLE 3

Preparation of (3)

1-(1H-1,2,4-triazol-1-yl)-2-isopropoxy-2-(2,4-dichlorophenyl)pentane (a) Preparation of the intermediate 1-(methylsulfonyloxy)-2-isopropoxy-2-(2,4-dichlorophenyl)-pentane 2.8 ml (35 mmoles) of methanesulfochloride are added dropwise, with cooling (ice bath), to a solution of 8.0 g (27 mmoles) of 2-(2,4-dichlorophenyl)-2-isopropoxypentan-1-ol and 0.1 g of 4-dimethylaminopyridine in 60 ml of absolute pyridine, the mixture is allowed to stand at room temperature for 16 hours and is concentrated, and diethyl ether is added to the residue. The diethyl ether phase is washed twice with ice-cold 2N hydrochloric acid and twice with half-saturated sodium chloride solution, dried over sodium sulfate, filtered and concentrated in vacuo. A small sample is purified by column chromatography (silica gel; 1:4 ethyl acetate/petroleum ether) for characterisation, and the resulting oil is induced to crystallise by adding petroleum ether. Colourless crystals of melting point 58°–61° C. are obtained.

| | | calculated | found |
|---|---|---|---|
| analysis [%] | C | 48.8 | 48.9 |
| | H | 6.0 | 6.1 |
| | S | 8.7 | 9.1 |
| | Cl | 19.2 | 19.1 |

(b) Preparation of the end product

The mesylate prepared in accordance with (a) is dissolved in 100 ml of absolute dimethyl sulfoxide, and 3.2 g (35 mmoles) of the sodium salt of 1,2,4-triazole are added. The reaction mixture is stirred for 8 hours at a bath temperature of 120° C. and is then cooled to room temperature and poured into ice water, and the mixture is extracted twice with ethyl acetate. The combined extracts are washed 4 times with half-saturated sodium chloride solution, dried over sodium sulfate, filtered and concentrated. The crude product is purified by column chromatography (silica gel; 1:1 ethyl acetate/petroleum ether) and affords a colourless oil. $n^{50}_D = 1.5299$. 100 MHz-$^1$H-NMR (CDCl$_3$): $\delta = 7.75$ and 7.65 ppm (s, 2H of triazole); 7.1–7.6 ppm (m, 2H, aromatic); 4.85 ppm (dd, 2H, CH$_2$-N); 4.0 ppm (m, 1H, —C$\underline{H}$(CH$_3$)$_2$); 0.8–2.6 ppm (m, 14H, —CH(C$\underline{H}_3$)$_2$, —C$\underline{H}_2$—C$\underline{H}_2$—CH$_3$);

| | | calculated | found |
|---|---|---|---|
| analysis [%] | C | 56.2 | 55.9 |
| | H | 6.2 | 6.0 |
| | N | 12.3 | 12.0 |
| | Cl | 20.7 | 20.5 |

EXAMPLE 4

Preparation of

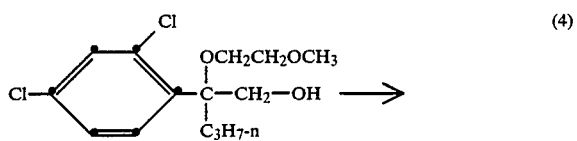

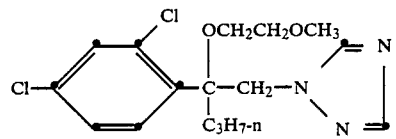

2-(1H-1,2,4-triazol-1-yl)-2-(2,4-dichlorophenyl)-2-(2-methoxyethyloxy)-pentane (a) Preparation of the intermediate 1-(methylsulfonyloxy)-2-(2-methoxyethoxy)-2-(2,4-dichlorophenyl)-pentane 1.4 g (4.6 mmoles) of 2-(2,4-dichlorophenyl)-2-(2-methoxyethoxy)-pentan-1-ol and 50 mg of 4-dimethylaminopyridine are dissolved in 10 ml of pyridine, and 0.43 ml (5.5 mmoles) of methanesulfochloride is added at room temperature. The reaction mixture is allowed to stand at room temperature for 16 hours and is then poured into ice water and extracted twice with diethyl ether. The combined ether extracts are washed twice with dilute, ice-cold hydrochloric acid and twice with half-saturated sodium chloride solution and are dried over sodium sulfate and filtered, and the filtrate is concentrated. The crude product (1.7 g = 100% of theory), which is obtained in the form of a yellowish, viscous oil, can be employed without purification in the next stage. A small sample is purified by column chromatography (silica gel; 1:3 ethyl acetate/petroleum ether, then 1:2) for characterisation. This gives a colourless, viscous oil of $n^{50}_D$ 1.5114. 60 MHz-$^1$H-NMR (CDCl$_3$): $\delta = 7.2–7.8$ ppm (m, 3H, aromatic); 4.75 ppm (dd, 2H, —C$\underline{H}_2$OSOCH$_3$); 3.5–3.8 ppm (broad s, 4H, —C$\underline{H}_2$C$\underline{H}_2$OC$\underline{H}_3$); 3.4 ppm (s, 3H, —OC$\underline{H}_3$); 2.9 ppm (s, 3$\underline{H}$, —OSO$_2$C$\underline{H}_3$); 0.8–2.4 ppm

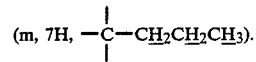

(m, 7H, —C—CH$_2$CH$_2$CH$_3$).

| | | calculated | found |
|---|---|---|---|
| analysis [%] | C | 46.8 | 46.2 |
| | H | 5.8 | 5.7 |
| | S | 8.3 | 8.0 |
| | Cl | 18.4 | 19.2 |
| | O | 20.8 | 20.7 |

(b) Preparation of the end product 12 g of the crude product prepared in (a) (starting from 30 mmoles of 2-(2,4-dichlorophenyl)-2-(2-methoxyethoxy)pentan-1-ol) are dissolved in 50 ml of absolute dimethyl sulfoxide, and 4 g (44 mmoles) of the sodium salt of 1,2,4-triazole are added. The mixture is stirred for 10 hours at a bath temperature of 120° C., the resulting dark solution is cooled to room temperature and poured into ice water, and the mixture is extracted twice with ethyl acetate. The combined extracts are washed with half-saturated sodium chloride solution, dried over sodium sulfate, filtered and concentrated. The residue is purified by column chromatography (silica gel); 1:2 to 4:1 ethyl acetate/petroleum ether) and affords 5.3 g (49.4% of theory for the 2 stages) of the end product in the form of a pale yellow oil of $n^{50}_D$ 1.5297. 60 MHz-hu 1H-NMR (CDCl$_3$): $\delta = 8.0$ ppm (s, 1H, triazol-H); 7.7 ppm (s, 1H, triazole-H); 7.0–7.6 ppm (m, 2H, aromatic); 4.85 ppm (dd, 2H, C$\underline{H}_2$-triazol); 3.6–4.0 ppm

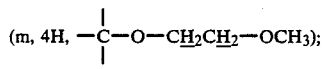(m, 4H, —C—O—CH₂CH₂—OCH₃);

3.5 ppm (s, 3H, —OCH₃); 0.7–2.7 ppm

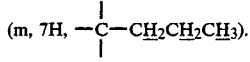(m, 7H, —C—CH₂CH₂CH₃).

|  |  | calculated | found |
|---|---|---|---|
| analysis [%] | C | 53.6 | 53.1 |
|  | H | 5.9 | 5.8 |
|  | N | 11.7 | 11.6 |
|  | Cl | 19.8 | 20.1 |

EXAMPLE 5

Preparation of

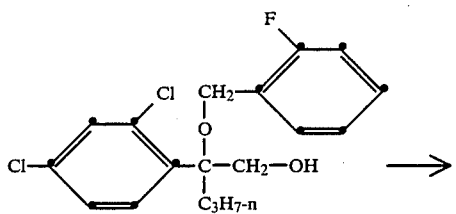 (5)

↓

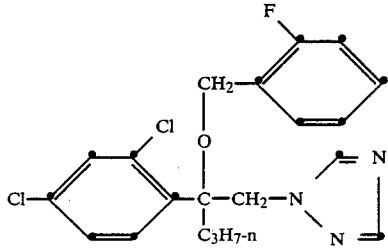

1-(1H-1,2,4-triazol-1-yl)-2-(2-fluorobenzyloxy)-2-(2,4-dichlorophenyl)-pentane (a) Preparation of the intermediate
1-(methylsulfonyloxy)-2-(2-fluorobenzyloxy)-2-(2,4-dichlorophenyl)-pentane 6.5 g of 2-(2,4-dichlorophenyl)-2-(2-fluorobenzyloxy)pentan-1-ol are dissolved in 15 ml of pyridine, and 2.5 g of methanesulfochloride are added. An exothermic reaction takes place, with the precipitation of pyridine hydrochloride, giving the mesylate, which is isolated analogously to Example 4 by extraction (with water and methylene chloride). Yield 8.16 g. 60 MHz-¹H-NMR (CDCl₃): δ=7.1–7.7 ppm (m, 6H, aromatic); 4.9 ppm (s, 2H, —CH₂—); 4.6 ppm (s, 2H, —CH₂—); 2.85 ppm (s, 3H, —CH₃); 2.0–2.5 ppm

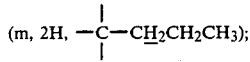(m, 2H, —C—CH₂CH₂CH₃);

0.7–1.6 ppm (m, 5H, —C—CH₂CH₂CH₃).

(b) Preparation of the end product

Reacting the mesylate prepared in (a) with the sodium salt of triazole (prepared from 0.6 g of sodium and 1.88 g of 1,2,4-triazole), after a procedure analogous to that of Example 4b, gives 2.4 g of the crude end product, which is purified analogously to Example 4 and affords 1.3 g of the pure end product in the form of a viscous oil. 60 MHz-¹HNMR (CDCl₃): δ=7.75 and 7.65 ppm (two s, 2H of triazole); 7.5–7.6 ppm (m, 6H, aromatic); 4.9 ppm (4 lines, AB spectrum, —CH₂—); 4.6 ppm (4 lines, AB spectrum, —CH₂—); 1.9–2.5 ppm (m, 2H, —C—CH₂CH₂CH₃); 0.7–1.5 ppm (m, 5H, —C—CH₂CH₂CH₃).

EXAMPLE 6

Preparation of

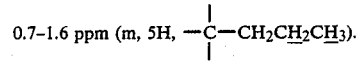 (6)

↓

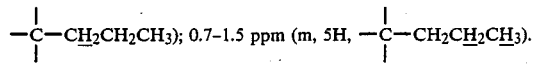

1-(1H-1,2,4-triazol-1-yl)-2-(n-butoxy)-2-(4-fluorophenyl)propane (a) Preparation of the intermediate
1-(methylsulfonyloxy)-2-(n-butoxy)-2-(4-fluorophenyl)-propane 3.42 g (15 mmoles) of 2-(4-fluorophenyl)-2-(n-butoxy)propan-1-ol are dissolved in 10 ml of pyridine, and 1.9 g (17 mmoles) of methanesulfochloride are added. The mesylate is formed in an exothermic reaction, with the precipitation of pyridine hydrochloride. The mesylate is extracted with ice water and chloroform, the organic phase is dried with Na₂SO₄, and the filtrate is concentrated in vacuo. The mesylate is obtained in the form of a viscous oil. 60 MHz-¹H-NMR (CDCl₃): δ=6.8–7.5 ppm (m, 4H, aromatic); 4.15 ppm (q, 2H, —CH₂OSO₂—); 2.9 ppm (s, 3H, —OSO₂CH₃).

(b) Preparation of the end product

The mesylate prepared in accordance with (a) is reacted with the sodium salt of 1,2,4-triazole. This is effected by dissolving 0.52 g (23 mmoles) of sodium in 20 ml of absolute methanol, and adding 1.55 g (23 mmoles) of 1,2,4-triazole to this solution. The methanol is then removed in vacuo, and the mesylate prepared in (a) is added, dissolved in 20 ml of dimethyl sulfoxide, to the crystalline residue. The mixture is heated for 6.5 hours at a bath temperature of 130° C. and is allowed to cool to room temperature, water is added and the mixture is extracted with chloroform. The combined extracts are washed with half-saturated sodium chloride solution, dried over sodium sulfate and filtered, and the filtrate is concentrated in vacuo. The 3.74 g of crude product obtained are purified by column chromatography (silica gel; 1:1 ethyl acetate/petroleum ether) and afford 1.57 g of the pure end product in the form of an oil. 60 MHz-$^1$H-NMR (CDCl$_3$): δ=8.10 and 7.85 ppm (2s, 2H of triazole); 6.9–7.4 ppm (m, 4H, aromatic); 4.3 ppm (s, 2H, —C$\underline{H}_2$N); 2.9–3.4 ppm (m, 2H, OC$\underline{H}_2$); 1.2–1.7 ppm

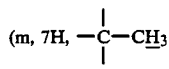

and OCH$_2$CH$_2$CH$_2$CH$_3$); 0.7–1.1 ppm (m, 3H, OCH$_2$CH$_2$CH$_2$C$\underline{H}_3$).

| analysis [%] | | calculated | found |
|---|---|---|---|
| | C | 65.0 | 65.3 |
| | H | 7.3 | 7.4 |
| | N | 15.2 | 15.0 |
| | F | 6.9 | 6.8 |

EXAMPLE 7

Preparation of

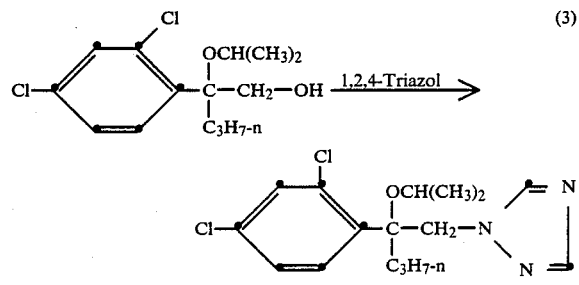

1-(1H-1,2,4-triazol-1-yl)-2-isopropoxy-2-(2,4-dichlorophenyl)-pentane

A solution of 5.5 g (30 mmoles) of dimethyl azodicarboxylate is added dropwise, at room temperature, to a solution of 5.8 g (20 mmoles) of 2-(2,4-dichlorophenyl)-2-isopropoxypentan-1-ol, 7.9 g (30 mmoles) of triphenylphosphine and 1.66 g (24 mmoles) of 1,2,4-triazole in 100 ml of absolute tetrahydrofuran, and the reaction mixture is then stirred for 3 hours at room temperature and then for a further 16 hours at 50° C. and is evaporated; the residue is digested with 100 ml of diethyl ether, the insoluble residue is filtered off, and the ether phase is concentrated again and purified by column chromatography (silica gel; 1:1 ethyl acetate/petroleum ether). This gives a colourless oil having physical data which agree entirely with those in Example 3b).

EXAMPLE 8

Preparation of

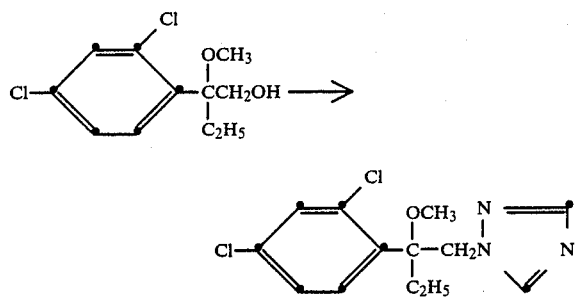

1-(1H-1,2,4-triazol-1-yl)-2-methoxy-2-(2,4-dichlorophenyl)-butane (a) Intermediate 1-(methylsulfonyloxy)-2-methoxy-2-(2,4-dichlorophenyl)-butane 6.75 g (59 mmoles) of methanesulfochloride, dissolved in 20 ml of tetrahydrofuran, are added dropwise, with cooling, at 20°–28° C. to a solution of 13.34 g (53 mmoles) of 2-(2,4-dichlorophenyl)-2-methoxybutan-1-ol and 5.95 g (59 mmoles) of triethylamine in 70 ml of tetrahydrofuran, triethylamine hydrochloride being precipitated immediately. After the salt has been filtered off with suction, and the solvent has been removed on a rotary evaporator, the crude product is dissolved in chloroform and washed twice with water. Drying the organic phase with Na$_2$SO$_4$ and concentrating it on a rotary evaporator at 60° C. and 20 mbar gives 17.4 g of a colourless oil in which no impurities can be discerned in a thin layer chromatogram. Refractive index n$^{50}_D$ 1.5247. 60 MHz-$^1$H-NMR (DCCl$_3$): δ=7.2–7.7 ppm (m, 34, aromatic); 4.5–5.1 ppm (m, 2H, OCH$_2$); 3.3 ppm (s, 3H, OCH$_3$); 2.9 ppm (s, 3H, OCH$_3$), 1.5–2.4 ppm (m, 2H, C$\underline{H}_2$CH$_3$); 0.7 ppm (t, 3H, CH$_2$C$\underline{H}_3$).

| | | calculated | found |
|---|---|---|---|
| analysis (%) | C | 44.1 | 44.6 |
| | H | 4.9 | 5.0 |
| | S | 9.8 | 9.7 |
| | Cl | 21.7 | 21.7 |

(b) End product 6.54 g (0.20 mole) of the mesylate prepared in (a) are reacted with the sodium salt of triazole (prepared from 0.58 g of sodium and 1.73 g of triazole as described in Example 2b) by heating for 4 hours in 40 ml of anhydrous dimethyl sulfoxide. Ethyl acetate is then added to the reaction mixture, and the latter is extracted 3 times with water. Drying the organic phase with Na$_2$SO$_4$ and removing the solvent on a rotary evaporator gives 6.04 g of oil as a crude product, and this, after purification by means of a silica gel column (1:1 ethyl acetate/petroleum ether mixture), gives 2.91 g (48.5%) of pure product. 2.85 g of this product are distilled at 115°–120° C. under a pressure of 0.03 mmHg; 2.74 g of colourless distillate are obtained. Refractive index n$^{50}_D$=1.5501. 60 MHz-$^1$H-NMR (DDCl$_3$): δ=7.63 and 7.70 ppm (2s, 2H, triazole), 7.0–7.5 ppm (m, 3H, aromatic); 4.5–5.3 ppm (m, 2H, CH$_2$N); 3.35 ppm (s, 3H, OCH$_3$); 1.9–2.7 ppm (m, 2H, CH$_2$CH$_3$); 0.80 ppm (t, 3H, CH$_2$CH$_3$).

| analysis (%) | | calculated | found |
|---|---|---|---|
| | C | 52.02 | 52.31 |
| | H | 5.04 | 5.00 |
| | N | 14.00 | 13.95 |
| | Cl | 23.62 | 23.93 |

EXAMPLE 9

Preparation of

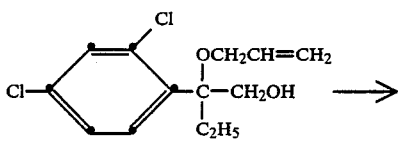

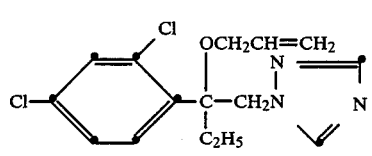

1-(1H-1,2,4-triazol-1-yl)-2-allyloxy-2-(2,4-dichlorophenyl)-butane (a) Intermediate
1-(methylsulfonyloxy)-2-allyloxy-2-(2,4-dichlorophenyl)-butane 2.28 g (0.02 mole) of methanesulfochloride dissolved in 10 ml of tetrahydrofuran are added dropwise at room temperature, with slight cooling, to a solution of 4.98 g (0.018 mole) of the alcohol of Example VIII and 2.01 g (0.02 mole) of triethylamine in 25 ml of tetrahydrofuran. After the precipitated triethylamine hydrochloride has been filtered off with suction, the filtrate is concentrated on a rotary evaporator and the crude product thus obtained is purified by chromatography on a silica gel column (mobile phase 3:1 petroleum ether/ethyl acetate). Removing the solvent on a rotary evaporator at a bath temperature of 60° and a pressure of 20 mbar gives 5.70 g (89.2%) of pure product in the form of a colourless oil. Refractive index $n^{50}_D$ 1.5224. 60 MHz-$^1$H-NMR (DCCl$_3$): δ=7.2–7.7 ppm (m, 3H, aromatic); 5.1–6.3 ppm (m, 3H, olefinic); 4.8 ppm (s, 2H, C—CH$_2$OSO$_2$); 3.7–4.2 ppm (m, 2H, OCH$_2$); 2.9 ppm (s, 3H, OSO$_2$CH$_3$); 1.7–2.4 ppm (m, 2H, CH$_2$CH$_3$); 0.75 ppm (t, 3H, CH$_2$CH$_3$).

| analysis (%) | | calculated | found |
|---|---|---|---|
| | C | 47.60 | 47.89 |
| | H | 5.14 | 5.20 |
| | S | 9.08 | 8.87 |
| | Cl | 20.07 | 19.88 |

(b) End product 5.32 g (0.0151 mole) of the mesylate prepared in (a) are reacted with the sodium salt of triazole (prepared from 1.20 g of triazole and 0.40 g of sodium in methanol as described in Example 2b) by stirring for 11 hours at 120° C. in 20 ml of anhydrous dimethyl sulfoxide. 500 ml of water are added, and the mixture is extracted with chloroform. After the organic phase has been dried with Na$_2$SO$_4$, the chloroform is removed on a rotary evaporator and the residue (4.58 g of oil) is purified by means of a silica gel column (mobile phase 2:1 to 1:1 petroleum ether/ethyl acetate). The solvent is removed from the pure fractions on a rotary evaporator to give 3.31 g (67.2%) of product in the form of a colourless oil. 60 MHz-$^1$H-NMR (DCCl$_3$): δ=7.73 and 7.65 ppm (2s, 2H, triazole); 6.9–7.4 ppm (m, 3H, aromatic); 5.0–6.4 ppm (m, 3H, olefinic); 4.5–5.1 ppm (m, 2H, NCH$_2$); 3.6–4.4 ppm (m, 2H, OCH$_2$); 1.8–2.6 ppm (m, 2H, CH$_2$CH$_3$); 0.8 ppm (t, 3H, CH$_2$CH$_3$).

| analysis (%) | | calculated | found |
|---|---|---|---|
| | C | 55.23 | 55.53 |
| | H | 5.25 | 5.48 |
| | N | 12.88 | 12.55 |
| | Cl | 21.74 | 21.16 |

EXAMPLE 10

Preparation of

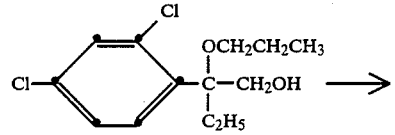

1-(1H-1,2,4-triazol-1-yl)-2-propoxy-2-(2,4-dichlorophenylbutane (a) Intermediate
1-(methylsulfonyloxy)-2-propoxy-2-(2,4-dichlorophenyl)-butane 4.78 g (0.017 mole) of the alcohol of Example IX in 50 ml of THF are reacted as before with 2.27 g (0.02 mole) of methanesulfochloride in the presence of 2.00 g (0.02 mole) of triethylamine. After the triethylamine hydrochloride has been filtered off with suction, the filtrate is concentrated, and the residue is purified by column chromatography (silica gel; 4:1 petroleum ether/ethyl acetate). 5.64 g (92.3%) of a colourless oil are obtained. 60 MHz-$^1$H-NMR (DCCl$_3$): δ=7.1–7.8 ppm (m, 3H, aromatic); 4.5–4.9 ppm (m, 2H, CH$_2$OS); 3.2–3.5 ppm (m, 2H, OCH$_2$); 2.8 ppm (s, 3H, OSO$_2$CH$_3$); 1.6–2.4 ppm (m, 4H, 2×CH$_2$); 0.6–1.3 ppm (m, 6H, 2×CH$_3$).

(b) End product 0.45 g (0.02 g atom) of sodium are dissolved in 20 ml of methanol. 1.35 g (0.02 mole) of triazole are then added, and the solution is concentrated to dryness. Residues of methanol are removed completely by concentrating twice with toluene on a rotary evaporator. The sodium salt of triazole thus obtained in 40 ml of anhydrous dimethyl sulfoxide is heated at 120° C. for 5 hours with 5.35 g (0.016 mole) of the mesylate prepared in (a). Working up by extraction with water and chloroform, followed by purification by chromatography using a silica gel column, gives 2.93 g (54.8%) of a colourless oil, which solidifies at room temperature. Recrystallisation from petroleum ether gives 2.43 g (45.4%) of colourless crystals, melting point 74°–75° C. 60 Mhz-¹H-NMR (DCCl₃): δ=7.72 and 7.62 ppm (2S, 2H, triazole); 7.0–7.5 ppm (m, 3H, aromatic); 4.5–5.1 ppm (m, 2H, CH₂N); 3.1–3.7 ppm (m, 2H, OCH₂); 1.4–2.8 ppm (m, 4H, 2×CH₃); 0.6–1.2 ppm (m, 6H, 2×CH₃).

EXAMPLE 11

Preparation of

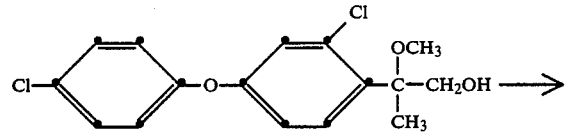

1-(1H-1,2,4-triazol-1-yl)-2-methoxy-2-[2-chloro-4-(4-chlorophenoxy)-phenyl]-propane (a) (Intermediate 1-(methylsulfonyloxy)-2-methoxy-2-[2-chloro-4-(4-chlorophenoxy)-phenyl]-propane 9.37 g (0.029 mole) of the alcohol of Example X are reacted, in the presence of 3.33 g (0.033 mole) of triethylamine, with 3.77 g (0.033 mole) of methanesulfochloride in 100 ml of tetrahydrofuran. After te triethylamine hydrochloride has been filtered off with suction, the filtrate is concentrated on a rotary evaporator to give 12.4 g of oily crude product. 7.91 g are purified by column chromatography (silica gel; 2 parts of petroleum ether and 1 part of etyl acetate) to give 6.89 g (93.1%) of pure mesylate in the form of a colourless oil. 60 MHz-¹H-NMR (DCCL₃): δ=6.8–7.6 ppm (m, 7H, aromatic); 4.3–4.7 ppm (m, 2H, CH₂OS); 3.23 ppm (s, 3H, OCH₃); 2.96 ppm (s, 3H, OSO₂CH₃); 1.78 ppm (s, 3H, C—CH₃).

| analysis (%) | | calculated | found |
|---|---|---|---|
| | C | 50.38 | 50.58 |
| | H | 4.48 | 4.72 |
| | S | 7.91 | 7.65 |
| | Cl | 17.50 | 17.11 |

(b) End product

The sodium salt of triazole is prepared from 0.46 g of sodium and 1.37 g of traizole in methanol, as described before. A solution of 6.69 g (0.0165 mole) of the mesylate prepared in (a) in 50 ml of anhydrous dimethyl sulfoxide is added, and the mixture is stirred for 9 hours at 120° C. The reaction mixture is extracted with chloroform and water to give, after removing the solvent, 6.87 g of crude product, which is purified by column chromatography (silica gel: 1 part of petroleum ether/1 part of ethyl acetate) and affords 3.23 g (51.8%) of pure product in the form of a colourless oil. 60 MHz-¹H-NMR (DCCl₃): δ=8.00 and 7.82 ppm (2S, 2H, triazole); 6.7–7.5 ppm (m, 7H, aromatic); 4.6 ppm (s, 2H, CH₂N); 3.2 ppm (s, 3H, OCH₃); 1.7 ppm (s, 3H, C—CH₃).

The substances of the formula I listed below are also obtained as described:

TABLE

Compounds of the formula $$R_1-\underset{\underset{R_2}{|}}{\overset{\overset{OR_3}{|}}{C}}-CH_2-N\begin{array}{c}\diagup\!\!=\!\!N\\ \diagdown_{N=\!\!\diagdown}\end{array}$$

73°

| Comp. No. | R₁ | R₂ | R₃ | Phys. Constant (°C.) (%) Analyses |
|---|---|---|---|---|
| 1 | C₆H₃Cl₂(2,4) | C₃H₇-n | CH₃ | B.P. 170–175°/0.04 mbar |
| 2 | C₆H₃Cl₂(2,4) | C₃H₇-n | C₂H₅ | M.P. 67° C. |
| 3 | C₆H₃Cl₂(2,4) | C₃H₇-n | CH(CH₃)₂ | $n_D^{50}$ 1.5299 |
| 4 | C₆H₃Cl₂(2,4) | C₃H₇-n | CH₂CH₂OCH₃ | $n_D^{50}$ 1.5297 |
| 5 | C₆H₃Cl₂(2,4) | C₃H₇-n | CH₂—C₆H₄F(2) | Cf. Preparation Ex. 5 |
| 6 | C₆H₄F(4) | CH₃ | C₄H₉-n | calculated found<br>C 65.0 65.3<br>H 7.3 7.4<br>N 15.2 15.0<br>F 6.9 6.8 |
| 7 | C₆H₄F(4) | C₂H₅ | C₄H₉-n | calculated found<br>C 66.0 66.2<br>H 7.6 7.5<br>N 14.4 14.5<br>F 6.5 6.1 |
| 8 | C₆H₄F(4) | C₂H₅ | CH₂CH=CHCH₃ | calculated found<br>C 66.4 65.5<br>H 6.9 6.9<br>N 14.5 14.8<br>F 6.6 6.6 |
| 9 | C₆H₄Cl(4) | C₃H₇-n | CH₂C₆H₅ | B.P. 170–176°/0.02 mbar |
| 10 | C₆H₃Cl₂(2,4) | CH₃ | CH₃ | calculated found<br>C 50.4 50.7<br>H 4.6 4.9<br>N 14.6 14.0 |
| 11 | C₆H₃Cl₂(2,4) | CH₃ | C₃H₇-n | M.P. 62–64° |
| 12 | C₆H₃Cl₂(2,4) | CH₃ | C₄H₉-n | B.P. 190–200°/0.02 mbar |
| 13 | C₆H₃(2,4) | CH₃ | CH₂CH=CH₂ | M.P. 68–70° |
| 14 | C₆H₃Cl₂(2,4) | CH₃ | CH—C(CH₃)=CH₂ | B.P. 165–175°/0.02 mbar |

TABLE-continued

Compounds of the formula $$R_1-\underset{R_2}{\overset{OR_3}{C}}-CH_2-N\underset{N=}{\overset{N=}{\diagdown}}$$

| Comp. No. | R₁ | R₂ | R₃ | Phys. Constant (°C.) (%) Analyses |
|---|---|---|---|---|
| 15 | C₆H₃Cl₂(2,4) | CH₃ | CH₂—[C₆H₅Cl(4)] | calculated found<br>C 54.5 54.6<br>H 4.1 4.2<br>N 10.6 10.5 |
| 16 | C₆H₃Cl₂(2,4) | C₂H₅ | CH₃ | B.P. 170–175°/0.04 mbar |
| 17 | C₆H₃Cl₂(2,4) | C₂H₅ | C₃H₇-n | B.P. 192–198°/0.03 mbar |
| 18 | C₆H₃Cl₂(2,4) | C₂H₅ | CH₂CH=CH₂ | calculated found<br>C 55.2 55.0<br>H 5.2 5.2<br>N 12.9 13.0<br>Cl 21.7 21.7 |
| 19 | C₆H₃Cl₂(2,4) | C₃H₇-n | C₃H₇-n | 60 MHz-¹HNR (CDCl₃): δ = 7.8 & 7.7 ppm (2s, 2H of the triazole); 6.9–6.5 ppm (m. 3H, aromatic); 4.8 ppm (4 lines AB spectrum, 2H,CH₂N); 3.1–3.7 ppm (m. 2H, OCH₂); 1.7–2.6 ppm (m, 12H. OCH₂CH₂CH₂CH₃und OCCH₂CH₂CH₃). |
| 20 | C₆H₃Cl₂(2,4) | C₃H₇-n | C₄H₉-n | B.P. 189–195°/0.02 mbar |
| 21 | C₆H₃Cl₂(2,4) | C₃H₇-n | CH₂CH=CH₂ | B.P. 200–210/0.02 mbar |
| 22 | C₆H₃Cl(2,4) | C₃H₇-n | CH₂CH=CHCH₃ | B.P. 180–190°/0.02 mbar |
| 23 | C₆H₃Cl₂(2,4) | C₃H₇-n | CH₂—C₆H₅ | calculated found<br>C 61.6 61.6<br>H 5.6 5.7<br>N 10.8 10.5<br>Cl 18.2 18.0 |
| 24 | C₆H₃Cl₂(2,4) | CH(CH₃)₂ | CH₃ | B.P. 158–162°/0.03 mbar |
| 25 | C₆H₃Cl₂(2.4) | C₅H₁₁-n | CH₃ | B.P. 255°/0.04 mbar |
| 26 | C₆H₃Cl₂(2,4) | Cyclohexyl | CH₃ | B.P. 200–210°/0.1 mbar |
| 27 | C₆H₃Br(4)Cl(2) | CH₃ | CH₃ | B.P. 230°/0.05 mbar |
| 28 | C₆H₃Br(4)Cl(2) | C₃H₇-n | CH₃ | |
| 29 | C₆H₃Cl(2)F(4) | C₃H₇-n | CH₃ | B.P. 190°/0.04 mbar |
| 30 | Cl—C₆H₄—O—C₆H₄— | CH₃ | CH₃ | $n_D^{50}$ 1.5653 |
| 31 | Cl—C₆H₄—O—C₆H₄— | C₂H₅ | CH₃ | calculated found<br>C 63.8 64.3<br>H 5.6 5.7<br>N 11.7 11.5<br>Cl 9.9 9.6 |
| 32 | C₆H₃F₂(2,4) | C₃H₇-n | CH₃ | B.P. 164–170°/0.025 mbar |
| 33 | C₆H₃Cl₂(2,4) | C₄H₉-n | CH₃ | B.P. 245–250°/0.05 mbar |
| 34 | C₆H₃Cl(2)F(4) | C₂H₅ | CH₃ | oil |
| 35 | C₆H₃Cl(2)F(4) | C₂H₅ | CH₂CH=CH₂ | oil |
| 36 | F—C₆H₄—O—C₆H₄— | C₂H₅ | CH₃ | M.P. 58–60° |
| 37 | Cl—C₆H₄—O—C₆H₃—Cl | C₂H₅ | CH₃ | $n_D^{50}$ 1.5689 |
| 38 | C₆H₅F₄ | C₆H₅F(4) | CH₃ | M.P. 98–100° |
| 39 | C₆H₃Cl₂(2,4) | C₆H₅ | CH₃ | M.P. 128–131° |
| 40 | C₆H₃Cl₂(2,4) | C₆H₅ | CH₂—C₆H₅ | M.P. 118–119° |
| 41 | C₆H₄Cl(4) | C₆H₅ | CH₃ | M.P. 126–127° |
| 42 | C₆H₄Cl(4) | C₆H₅ | CH₂—C₆H₅ | M.P. 116–119° |
| 43 | C₆H₃Cl₂(2,4) | C₆H₅ | CH₂CH=CH₂ | M.P. 130–132° |

TABLE-continued

Compounds of the formula

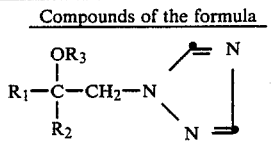

73°

| Comp. No. | R₁ | R₂ | R₃ | Phys. Constant (°C.) (%) Analyses |
|---|---|---|---|---|
| 44 | C₆H₄Cl(4) | Cyclohexyl | CH₃ | M.P. 118–119° |
| 45 | C₆H₄Cl(4) | Cyclohexyl | CH₂—C₆H₅ | M.P. 116–118° |
| 46 | C₆H₄F(4) | Cyclohexyl | CH₃ | M.P. 100–101° |
| 47 | C₆H₅ | Cyclopropyl | CH₃ | oil |
| 48 | C₆H₄F(4) | Cyclohexyl | CH₂C₆H₅ | M.P. 74–75° |
| 49 | C₆H₃Cl₂(2,4) | C₃H₇-n | CH₂—C₆H₅ | oil |
| 50 | C₆H₄Cl(4) | C₃H₇-n | CH₃ | B.P. 245–250°/0.5 mbar |
| 51 | C₆H₃Cl(2)F(4) | C₃H₇-n | CH₂C₆H₅ | oil |
| 52 | C₆H₄Cl(4) | C₄H₉-n | CH₃ | B.P. 185–195°/0.01 mbar |
| 53 | C₆H₅ | (CH₃)₃C | CH₃ | B.P. 150–160°/0.1 mbar |
| 54 | C₆H₅ | CH(CH₃)₂ | CH₃ | B.P. 250°/0.04 mbar |
| 55 | C₆H₅ | CH(CH₃)₂ | CH₂—C₆H₅ | B.P. 250°/0.04 mbar |
| 56 | C₆H₄CH₃(4) | C₄H₉-n | CH₃ | B.P. 170–180°/0.5 mbar |
| 57 | C₆H₅ | Cyclopentyl | CH₃ | M.P. 91–92° |
| 58 | C₆H₅ | Cyclohexyl | CH₃ | B.P. 190–200°/0.01 mbar |
| 59 | C₆H₅CH₂ | C₆H₅Cl(4) | CH₃ | M.P. 88–90° |
| 60 | C₆H₃Cl₂(2,4) | Cyclohexyl | CH₃ | B.P. 200–210°/0. mbar |
| 61 | C₆H₃Cl(2)F(4) | CH₃ | CH₂C₆H₅ | B.P. 250°/0.04 mbar |
| 62 | C₆H₃Cl(2)Br(4) | CH₃ | CH₂CH_CH5 | B.P. 219°/0.02 mbar |
| 63 | C₆H₃Cl₂(2,4) | CH₃ | CH₂CH=CHCH₃ | B.P. 190–200°/0.02 mbar |
| 64 | C₆H₃Cl₂(2,4) | C₃H₇-n | CH₂—C=CH₂<br>\|<br>CH₃ | B.P. 170–180°/0.02 mbar |
| 65 | C₆H₃Cl₂(2,4) | C₃H₇-n | CH₂CH=CHCH₃ | B.P. 180–190°/0.02 mbar |
| 66 | C₆H₃Cl(2)F(4) | C₃H₇-n | CH₂—CH=CH₂ | B.P. 210°/0.04 mbar |
| 67 | C₆H₃Cl(2)F(4) | C₃H₇-n | C₃H₇-n | B.P. 208°/0.04 mbar |
| 68 | C₆H₃Cl₂(2,4) | C₂H₅ | C₃H₇-n | B.P. 192–175°/0.03 mbar |
| 69 | C₆H₃Cl₂(2,4) | C₃H₇-n | CH₂CH(CH₃)CH₃ | viscous oil |
| 70 | C₆H₃Cl₂(2,4) | C₃H₇-n | CH(CH₃)₂ | $n_D^{50}$ 1.5299 |
| 71 | C₆H₃Cl(2)Br(4) | C₃H₇-n | CH₂C₆H₅ | oil |
| 72 | C₆H₃Cl(2)Br(4) | C₃H₇-n | CH₂CH=CH—CH₃ | B.P. 195–198°/0.01 mbar |
| 73 | C₆H₃Cl(2)Br(4) | C₃H₇-n | CH₃ | B.P. 178–185°/0.02 mbar |
| 74 | C₆H₃Cl(2)Br(4) | C₃H₇-n | C₄H₉-n | B.P. 167–174°/0.01 mbar |
| 75 | C₆H₄(OC₆H₅)(4) | C₂H₅ | CH₃ | oil |
| 76 | C₆H₄(OC₆H₅)(4) | C₂H₅ | CH₂CH=CH₂ | oil |
| 77 | C₆H₄(OC₆H₅)(4) | C₂H₅ | C₃H₇-n | oil |
| 78 | C₆H₃Cl(2)F(4) | CH₃ | CH₃ | B.P. 197–206°/0.016 mbar |
| 79 | C₆H₅ | C₃H₇-n | CH₃ | oil |
| 80 | C₆H₅ | C₃H₇-n | CH₂C₆H₅ | oil |
| 81 | C₆H₅ | C₄H₉-n | CH₃ | oil |
| 82 | C₆H₅ | C₆H₅ | CH₂CH=CH₂ | oil |
| 83 | C₆H₄F(4) | Cyclobutyl | CH₃ | oil |
| 84 | C₆H₄Cl(4) | C₁₁H₂₃-n | CH₃ | oil |
| 85 | C₆H₄Cl(4) | C₁₁H₂₃-n | CH₂C₆H₅ | B.P. 250/0.04 mbar |
| 86 | C₆H₃Cl₂(2,4) | CH₃ | CH₃ | oil |
| 87 | C₆H₃Cl₂(2,4) | C₃H₇-n | C₃H₇-n | oil |
| 88 | C₆H₃Cl₂(2,4) | CH₃ | C₄H₉-n | oil |
| 89 | C₆H₃Cl₂(2,4) | C₃H₇-n | CH₂CH=CH₂ | oil |
| 90 | C₆H₃Cl₂(2,4) | CH₃ | CH₂C₆H₅ | oil |
| 91 | C₆H₃Cl₂(2,4) | CH₃ | CH₂C₆H₄Cl(4) | oil |
| 92 | C₆H₃Cl₂(2,4) | C₃H₇-n | CH₂C₆H₅ | oil |
| 93 | C₆H₅—CH₂ | C₃H₇-n | CH₃ | oil |
| 94 | C₆H₅—CH₂ | C₃H₇-n | CH₂C₆H₅ | oil |
| 95 | C₆H₃Cl(2)Br(4) | CH₃ | CH₃ | oil |
| 96 | F(2)C₆H₃—CH₂ | C₄H₉-t | CH₃ | oil |
| 97 | C₆H₄Cl(4) | C₆H₅ | CH₂≡CH | oil |
| 98 | C₆H₃Cl₂(2,4) | C₃H₇-n | C₃H₇-n | oil |
| 99 | C₆H₄F(4) | C₂H₅ | C₄H₉-n | oil |
| 100 | C₆H₄F(4) | C₂H₅ | CH₂CH=CHCH₃ | oil |
| 101 | C₆H₃Cl₂(2,4) | C₂H₅ | CH₂CH=CH₂ | viscous oil |
| 102 | C₆H₄F(4) | C₂H₅ | CH₃ | viscous oil |
| 103 | C₆H₃Cl(2)F(4) | C₂H₅ | C₃H₇-n | $n_D^{49}$ 1.5125 |
| 104 | C₆H₃Br(4)Cl(2) | C₂H₅ | C₄H₉-n | M.P. 72–73° |
| 105 | C₆H₃Cl₂(2,4) | C₂H₅ | CH₂—C(CH₃)=CH₂ | oil |

TABLE-continued

Compounds of the formula $$R_1-\underset{\underset{R_2}{|}}{\overset{\overset{OR_3}{|}}{C}}-CH_2-N\begin{array}{c}\diagup N\\ \diagdown N\end{array}$$

| Comp. No. | R$_1$ | R$_2$ | R$_3$ | Phys. Constant (°C.) (%) Analyses |
|---|---|---|---|---|
| 106 | Cl—⟨○⟩(Cl)—O—⟨○⟩ | C$_2$H$_5$ | CH$_3$ | oil |
| 107 | Cl—⟨○⟩—O—⟨○⟩ | C$_3$H$_7$-i | CH$_3$ | M.P. 142–143° |
| 108 | Br—⟨○⟩—O—⟨○⟩(Cl) | C$_2$H$_5$ | CH$_3$ | oil |
| 109 | Cl—⟨○⟩—O—⟨○⟩(Cl) | C$_3$H$_7$-n | CH$_2$CH=CH$_2$ | M.P. 89–90° |
| 110 | Cl—⟨○⟩—O—⟨○⟩(Cl) | C$_3$H$_7$-n | CH$_3$ | $n_D^{50}$ 1.5595 |
| 111 | Cl—⟨○⟩—O—⟨○⟩(Cl) | C$_2$H$_5$ | CH$_2$CH=CH$_2$ | $n_D^{50}$ 1.5662 |
| 112 | Cl—⟨○⟩—O—⟨○⟩(Cl) | C$_2$H$_5$ | CH$_2$—C(CH$_3$)=CH$_2$ | $n_D^{50}$ 1.5610 |
| 113 | Cl—⟨○⟩—O—⟨○⟩(Cl) | CH$_3$ | CH$_2$—CH$_2$=CH$_2$ | $n_D^{50}$ 1.5689 |
| 114 | Cl—⟨○⟩—O—⟨○⟩(Cl) | CH$_3$ | CH$_3$ | $n_D^{50}$ 1.5765 |
| 115 | Cl—⟨○⟩—O—⟨○⟩(CH$_3$) | CH$_3$ | CH$_3$ | $n_D^{50}$ 1.5738 |

TABLE-continued

Compounds of the formula $$R_1-\underset{R_2}{\overset{OR_3}{\underset{|}{C}}}-CH_2-N\underset{N}{\overset{N}{\diagup}}$$

| Comp. No. | R₁ | R₂ | R₃ | Phys. Constant (°C.) (%) Analyses |
|---|---|---|---|---|
| 116 | 4-Cl-C₆H₄-O-C₆H₄- (with CH₃) | CH₃ | CH₂—CH=CH₂ | $n_D^{50}$ 1.5695 |
| 117 | 4-Cl-C₆H₄-O-C₆H₄- (with CH₃) | C₂H₅ | CH₃ | M.P. 91–92° |
| 118 | 4-Cl-C₆H₄-O-C₆H₄- (with Cl) | C₂H₅ | CH₂C₃H₇-i | $n_D^{50}$ 1.5503 |
| 119 | 4-Cl-C₆H₄-O-C₆H₄- (with CH₃) | C₃H₇-n | CH₂—CH=CH₂ | $n_D^{50}$ 1.5594 |
| 120 | 4-Cl-C₆H₄-O-C₆H₄- (with CH₃) | C₂H₅ | CH₃ | $n_D^{50}$ 1.5601 |
| 121 | 4-Cl-C₆H₄-O-C₆H₄- (with CH₃) | C₂H₅ | CH₂—CH=CH₂ | $n_D^{50}$ 1.5570 |
| 122 | 4-Cl-C₆H₄-O-C₆H₄- (with Cl) | C₃H₇-n | C₃H₇-n | $n_D^{50}$ 1.5540 |
| 123 | 4-Cl-C₆H₄-O-C₆H₄- (with Cl) | C₂H₅ | C₃H₇-n | $n_D^{50}$ 1.5518 |
| 124 | 4-Cl-C₆H₄-O-C₆H₄- (with Cl) | CH₃ | C₃H₇-n | $n_D^{50}$ 1.5595 |

TABLE-continued

Compounds of the formula $$R_1-\underset{\underset{R_2}{|}}{\overset{\overset{OR_3}{|}}{C}}-CH_2-N\diagdown\underset{N}{\overset{N}{\diagup}}\rceil$$ 73°

| Comp. No. | $R_1$ | $R_2$ | $R_3$ | Phys. Constant (°C.) (%) Analyses |
|---|---|---|---|---|
| 125 | Cl—⟨phenyl⟩—O—⟨phenyl⟩— | $CH_3$ | $CH_3$ | $C_3H_7$-n | M.P. 97–98° |

Examples of formulations of active ingredients of the formula Ia (% = percent by weight)

| Emulsion concentrates/wettable powders | (a) | (b) | (c) |
|---|---|---|---|
| Active ingredient from Table 1 | 25% | 40% | 50% |
| Ca dodecylbenzenesulfonate | 5% | 8% | 6% |
| Castor oil polyethylene glycol ether (36 moles of ethylene oxide) | 5% | — | — |
| Tributylphenyl polyethylene glycol ether (30 moles of ethylene oxide) | — | 12% | 4% |
| Cyclohexanone | — | 15% | 20% |
| Mixed xylenes | 65% | 25% | 20% |

Emulsions of any desired concentration can be prepared from such concentrates by dilution with water. Wettable powders are obtained if the xylene component is replaced by silica and/or kaolin.

| Solutions | (a) | (b) | (c) | (d) |
|---|---|---|---|---|
| Active ingredient from Table 1 | 80% | 10% | 5% | 95% |
| Ethylene glycol monomethyl ether | 20% | — | — | — |
| Polyethylene glycol MW 400 | — | 70% | — | — |
| N-methyl-2-pyrrolidone | — | 20% | — | — |
| Epoxidised coconut oil | — | — | 1% | 5% |
| Petroleum ether (boiling range 160–190° C.) | — | — | 94% | — |

(MW = molecular weight)

The solutions are suitable for application in the form of very fine drops.

| Granules | (a) | (b) |
|---|---|---|
| Active ingredient from Table 1 | 5% | 10% |
| Kaolin | 94% | — |
| Highly disperse silica | 1% | — |
| Attapulgite | — | 90% |

The active ingredient is dissolved in methylene chloride, the solution is sprayed onto the carrier, and the solvent is then removed by evaporation in vacuo.

| Dusts | (a) | (b) |
|---|---|---|
| Active ingredient from Table 1 | 2% | 5% |
| Highly disperse silica | 1% | 5% |
| Talc | 97% | — |
| Kaolin | — | 90% |

Dusts ready for use are obtained by mixing the active ingredient intimately with the carriers.

Biological examples

Example 2.1

Action against Puccinia graminis on wheat (a) Residual protective action 6 days after sowing, wheat plants were sprayed with a spray liquor (0.002% of active substance) prepared from a wettable powder of the active ingredient. After 24 hours the treated plants were infested with a uredospore suspension of the fungus. After being incubated for 48 hours at 95–100% relative humidity and approx. 20° C., the infested plants were placed in a greenhouse at approx. 22° C. The development of rust pustules was assessed 12 days after infestation.

(b) Systemic action 5 days after sowing, wheat plants were watered with a spray liquor (0.006% of active substance, based on the volume of soil) prepared from a wettable powder of the active ingredient. After 48 hours the treated plants were infested with a uredospore suspension of the fungus. After being incubated for 48 hours at 95–100% relative humidity and approx. 20° C., the infested plants were placed in a greenhouse at approx. 22° C. The development of rust pustules was assessed 12 days after infestation.

Compounds from Table I exhibited a good action against Puccinia fungi. Untreated, but infested, control plants exhibited a 100% attack by Puccinia. Inter alia, compounds Nos. 30, 31, 36, 37 and 103 to 115 inhibited attack by Puccinia to 0 to 5%.

Example 2.2

Action against Cercospora arachidicole on groundnut plants

Residual protective action

Groundnut plants 10–15 cm high were sprayed with a spray liquor (0.006% of active substance) prepared from a wettable powder of the active substance, and 48 hours later were infested with a conidia suspension of the fungus. The infested plants were incubated for 72 hours at approx. 21° C. and a high humidity and were then placed in a greenhouse until the typical leaf spots appeared.

The fungicidal action is assessed 12 days after infestation, on the basis of the number and size of the spots which have appeared.

In comparison with untreated, but infested, control plants (number and size of spots = 100%), groundnut plants which had been treated with active ingredients from Table I exhibited a considerably reduced attack by Cercospora. Thus compounds Nos. 30, 31, 36, 37 and 103 to 115 prevented the appearance of spots in the above test almost completely (0 to 10%).

Example 2.3

Action against Erysiphe graminis on barley (a) Residual protective action

Barley plants approx. 8 cm high were sprayed with a spray liquor (0.002% of active subtance) prepared from a wettable powder of the active ingredient. After 3-4 hours the treated plants were dusted with conidia of the fungus. The infested barley plants were placed in a greenhouse at approx. 22° C., and the fungal attack was assessed after 10 days.

(b) Systemic action

Barley plants approx. 8 cm high were watered with a spray liquor (0.0006% of active substance, based on the volume of soil) prepared from a wettable powder of the active ingredient. In doing so, care was taken that the spray liquor did not come in contact with the parts of the plants above ground. After 48 hours the treated plants were dusted with conidia of the fungus. The infested barley plants were placed in a greenhouse at approx. 22° C., and the fungal attack was assessed after 10 days.

Compounds of the formula I exhibited a good action against Erysiphe fungi. Untreated, but infested, control plants exhibited a 100% attack by Erysiphe. Amongst other compounds from Table I, compounds Nos. 30, 31, 36, 37 and 103 to 115 inhibited the fungal attack on barley to 0 to 5%. Compounds Nos. 32, 36 and 37 were particularly effective (no attack).

Example 2.4

Residual protective action against *Venturia inaequalis* on apple shoots

Apple cuttings having fresh shoots 10-20 cm long were sprayed with a spray liquor (0.006% of active substance) prepared from a wettable powder of the active ingredient. After 24 hours the treated plants were infested with a conidia suspension of the fungus. The plants were then incubated for 5 days at 90-100% relative humidity and were placed in a greenhouse at 20°-24° C. for a further 10 days. The attack of scab was assessed 15 days after infestation. Control plants suffered 100% attack. Compounds Nos. 30, 31, 36, 37 and 103 to 115 inhibited the attack of the disease to less than 10%. No attack at all took place when treatment was carried out with active ingredients Nos. 32, 36, 37, 109, 111, 114, 115 and 120.

Example 2.5

Action against *Brotrytis cinerea* on apples

Residual protective action

Artificially damaged apples were treated by dropwise addition of a spray liquor (0.02% of active substance) prepared from a wettable powder of the active substance to the damaged areas. The treated fruits were then inoculated with a spore suspension of *Botrytis cinerea* and were incubated for 1 week at a high humidity and approx. 20° C. The presence and the size of areas of decay on the fruit were used to assess the fungicidal activity. When treatment was carried out with compounds Nos. 30, 31, 36, 37 and 103 to 115, virtually no areas of decay, or none at all, were observed (0-5% attack).

What is claimed is:

1. A compound of formula Ia

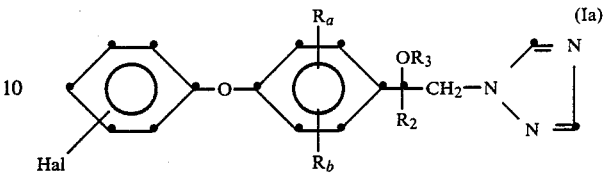

in which Hal is halogen;

$R_a$ and $r_b$ independently of one another are hydrogen, halogen, $C_1-C_6$-halogenoalkyl, $C_1-C_6$-halogenoalkoxy, $C_1-C_6$-alkoxy, $C_1-C_6$-alkyl, nitro and/or cyano, with the proviso that at least one of $R_a$ and $R_b$ is not hydrogen;

$R_2$ is $C_1-C_{12}$-alkyl, $C_1-C_6$-alkyl which is substituted by $C_1-C_6$-alkoxy or $C_3-C_8$-cycloalkyl, $C_3-C_8$-cycloalkyl, phenyl which is unsubstituted or monosubstituted to trisubstituted by halogen, $C_1-C_6$-halogenoalkyl, $C_1-C_6$-halogenoalkoxy, $C_1-C_6$ alkoxy, $C_1-C_6$-alkyl, phenoxy, halogenophenoxy, phenyl, benzyl, halogenobenzyl, nitro and/or cyano, or benzyl which is unsubstituted or monosubstituted to trisubstituted by halogen, $C_1-C_6$-halogenoalkyl, $C_1-C_6$-alkoxy, $C_1-C_6$-alkyl, nitro and/or cyano; and $R_3$ is $C_1-C_6$-alkyl which is unsubstituted or substituted by $C_1-C_3$-alkoxy, or is $C_3-C_4$-alkenyl, benzyl or halogenobenzyl.

2. A compound of the formula Ia according to claim 1, wherein Hal is fluorine, chlorine or bromine; $R_a$ and $R_b$ independently of one another are hydrogen, halogen, $C_1-C_3$-halogenoalkyl, $C_1-C_3$-halogenoalkoxy, $C_1-C_3$-alkoxy, $C_1-C_3$-alkyl, nitro or cyano; $R_2$ is $C_1-C_6$-alkyl; and $R_3$ is $C_1-C_6$-alkyl which is unsubstituted or substituted by $C_1-C_3$-alkoxy, or is $C_3-C_4$-alkenyl, benzyl or halogenobenzyl.

3. A compound according to claim 1 selected from the following group consisting of:

1-(1H-1,2,4-triazol-1-yl)-2-methoxy-2-[4-(4-chlorophenoxy)-2-chlorophenyl]-butane;

1-(1H-1,2,4-triazol-1-yl)-2-allyloxy-2-[4-(4-chlorophenoxy)-2-chlorophenyl]-pentane;

1-(1H-1,2,4-triazol-1-yl)-2-methoxy-2-[4-(4-chlorophenoxy)-2-chlorophenyl]-pentane;

1-(1H-1,2,4-triazol-1-yl)-2-allyloxy-2-[4-(4-chlorophenoxy)-2-chlorophenyl]-butane;

1-(1H-1,2,4-triazol-1-yl)-2-(2-methylallyloxy)-2-[4-(4-chlorophenoxy)-2-chlorophenyl]-butane;

1-(1H-1,2,4-triazol-1-yl)-2-allyloxy-2-[4-(4-chlorophenoxy)-2-chlorophenyl]-propane;

1-(1H-1,2,4-triazol-1-yl)-2-methoxy-2-[4-(4-chlorophenoxy)-2-chlorophenyl]-propane;

1-(1H-1,2,4-triazol-1-yl)-2-methoxy-2-[4-(4-chlorophenoxy)-2-methylphenyl]-propane;

1-(1H-1,2,4-triazol-1-yl)-2-allyloxy-2-[4-(4-chlorophenoxy)-2-methylphenyl]-propane;

1-(1H-1,2,4-triazol-1-yl)-2-methoxy-2-[4-(4-chlorophenoxy-2-methylphenyl]-butane;

1-(1H-1,2,4-triazol-1-yl)-2-(2-methylpropoxy)-[4-(4-chlorophenoxy)-2-chlorophenyl]-butane;

1-(1H-1,2,4-triazol-1-yl)-2-allyloxy-2-[4-(4-chlorophenoxy)-2-methylphenyl]-pentane;

1-(1H-1,2,4-triazol-1-yl)-2-methoxy-2-[4-(4-chlorophenoxy)-2-methylphenyl]-butane;

1-(1H-1,2,4-triazol-1-yl)-1-allyloxy-2-[4-(4-chlorophenoxy)-2-methylphenyl]-butane;

1-(1h-1,2,4-triazol-1-yl)-2-propoxy-2-[4-(4-chlorophenoxy)-2-chlorophenyl]-pentane;

1-(1H-1,2,4-triazol-1-yl)-2-n-propoxy-2-[4-(4-chlorophenoxy)-2-chlorophenyl]-butane;

1-(1H-1,2,4-triazol-1-yl)2-n-propxy-2-[4-(4-chlorophenoxy)-2-chlorophenyl]-propane;

1-(1H-1,2,4-triazol-1-yl)2-n-propoxy-2-[4-(4-chlorophenoxy)-2-methylphenyl]-propane.

4. A compound of the formula

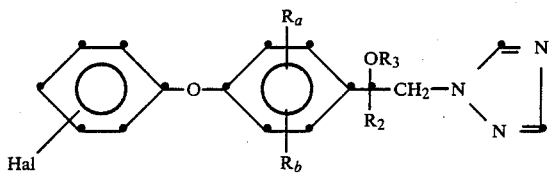

wherein

Hal is chlorine, fluorine or bromine;

$R_a$ and $R_b$ are hydrogen, $C_1-C_6$-alkyl or halogen;

$R_2$ is $C_1-C_6$ alkyl; and $R_3$ is $C_1-C_4$-alkyl;

with the proviso that at least one of $R_a$ and $R_b$ is not hydrogen.

5. A compound of the formula

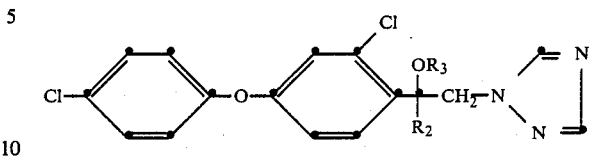

wherein $R_2$ represents methyl, ethyl, n-propyl, and $R_3$ represents methyl, n-propyl, allyl and, if $R_2$ represents ethyl, $R_3$ also represents 2-methyl-propyl of methylallyl.

6. 1-(1H-1,2,4-triazol-1-yl)-2-methoxy-2-[4-(4-chlorophenoxy)-2-chlorophenyl]]-butane according to claim 5.

7. 1-(1H-1,2,4-triazol-1-yl)-2-allyloxy-2-[4-(4-chlorophenoxy)-2-chlorophenyl]-butane according to claim 5.

8. 1-(1H-1,2,4-triazol-1-yl)-2-allyloxy-2-[4-(4-chlorophenoxy)-2-chlorophenyl]-propane according to claim 5.

9. A microbicidal composition which contains 0.1 to 99% of a compound according to claim 1, 99.9 to 1% of solid or liquid additives and 0.1 to 25% of a surfactant.

10. A process for controlling phytopathogenic microorganisms, which comprises applying 10 g to 5 kg of a compound according to claim 1 per hectare of cultivated area.

* * * * *